United States Patent
Hawthorne et al.

(10) Patent No.: US 9,489,487 B2
(45) Date of Patent: *Nov. 8, 2016

(54) BIO-INFORMATION SENSOR MONITORING SYSTEM AND METHOD

(75) Inventors: Jeffrey Scott Hawthorne, Bennett, CO (US); Michael Leonard Iiams, Littleton, CO (US); Glenn Charles Tubb, Englewood, CO (US); Richard A. Stoll, Morrison, CO (US); Gary Alan Shoffner, Westminster, CO (US); Brian Kirby Phillips, Lakewood, CO (US)

(73) Assignee: Alcohol Monitoring Systems, Inc., Littleton, CO (US)

(*) Notice: Subject to any disclaimer, the term of this patent is extended or adjusted under 35 U.S.C. 154(b) by 1272 days.

This patent is subject to a terminal disclaimer.

(21) Appl. No.: 11/086,192

(22) Filed: Mar. 22, 2005

(65) Prior Publication Data

US 2005/0163293 A1    Jul. 28, 2005

Related U.S. Application Data

(62) Division of application No. 10/441,960, filed on May 19, 2003, now Pat. No. 7,311,665.

(51) Int. Cl.
| | |
|---|---|
| *H04M 11/00* | (2006.01) |
| *G06F 15/16* | (2006.01) |
| *G06Q 10/00* | (2012.01) |
| *G06Q 50/00* | (2012.01) |
| *G06F 19/00* | (2011.01) |
| *A61B 5/00* | (2006.01) |

(52) U.S. Cl.
CPC ......... *G06F 19/3412* (2013.01); *A61B 5/0022* (2013.01); *G06F 19/3418* (2013.01); *Y10S 128/92* (2013.01)

(58) Field of Classification Search
None
See application file for complete search history.

(56) References Cited

U.S. PATENT DOCUMENTS

| 2,845,226 A | 7/1958 | Cummings et al. ...... 235/117 R |
| 3,439,596 A | 4/1969 | Pickering et al. ............ 396/301 |

(Continued)

FOREIGN PATENT DOCUMENTS

WO    WO 02/12883 A1    2/2002

OTHER PUBLICATIONS

Kristine K. Rapillo, Office Action (Non-Final), Dec. 23, 2011, U.S. Appl. No. 11/104,810 Titled "Bio-Information Sensor Monitoring System and Method", filed Apr. 13, 2005.

(Continued)

*Primary Examiner* — Fonya Long
*Assistant Examiner* — Kristine Rapillo
(74) *Attorney, Agent, or Firm* — Stanley J. Gradisar Attorney At Law, LLC; Stanley J. Gradisar

(57) ABSTRACT

A bio-information monitoring system passively monitors a patient with a remote portable bio-information unit that takes various bio-information measurements at selected time intervals as well as at random times without patient intervention. The measurements are converted to digital signals which are transmitted from the bio-information unit to a modem when the bio-information unit is in proximity to the modem. The signals are stored in the modem and uploaded to a central monitoring network. Automatic alerts may be sent from the central monitoring network to a treatment provider. The treatment provider may also access the information through secured dedicated websites via the Internet.

25 Claims, 5 Drawing Sheets

(56) References Cited

U.S. PATENT DOCUMENTS

| | | | |
|---|---|---|---|
| 4,173,971 | A | 11/1979 | Karez |
| 4,749,553 | A | 6/1988 | Lopez et al. ............... 422/84 |
| 4,868,545 | A | 9/1989 | Jones |
| 4,885,571 | A | 12/1989 | Pauley et al. ............. 340/573.4 |
| 4,916,435 | A | 4/1990 | Fuller |
| 4,999,613 | A | 3/1991 | Williamson et al. ...... 340/573.4 |
| 5,033,293 | A | 7/1991 | Honma et al. |
| 5,115,223 | A | 5/1992 | Moody ..................... 340/573.1 |
| 5,220,919 | A | 6/1993 | Phillips et al. ............... 600/345 |
| 5,303,575 | A | 4/1994 | Brown et al. |
| 5,408,520 | A * | 4/1995 | Clark ................. H04W 88/02 379/93.07 |
| 5,543,780 | A | 8/1996 | McAuley et al. ......... 340/572.1 |
| 5,627,520 | A | 5/1997 | Grubbs et al. ............. 340/572.1 |
| 5,678,562 | A | 10/1997 | Sellers |
| 5,724,025 | A | 3/1998 | Tavori |
| 5,823,409 | A | 10/1998 | Kennedy .................... 224/175 |
| 5,836,993 | A | 11/1998 | Cole |
| 5,944,661 | A | 8/1999 | Swette et al. ............... 600/345 |
| 5,982,281 | A | 11/1999 | Layson, Jr. |
| 6,024,699 | A | 2/2000 | Surwit et al. |
| 6,093,146 | A | 7/2000 | Filangeri |
| 6,168,563 | B1 * | 1/2001 | Brown ................. A61B 5/0002 128/904 |
| 6,364,834 | B1 * | 4/2002 | Reuss ................. A61B 5/0205 128/903 |
| 6,409,675 | B1 | 6/2002 | Turcott |
| 6,443,890 | B1 | 9/2002 | Schulze et al. |
| 6,497,655 | B1 | 12/2002 | Linberg et al. |
| 6,524,239 | B1 | 2/2003 | Reed et al. |
| 6,639,516 | B1 | 10/2003 | Copley |
| 6,726,636 | B2 | 4/2004 | Der Ghazarian et al. |
| 6,801,137 | B2 | 10/2004 | Eggers |
| 6,805,667 | B2 | 10/2004 | Christopherson et al. ... 600/300 |
| 6,924,750 | B2 | 8/2005 | Flick |
| RE38,838 | E | 10/2005 | Taylor, Jr. |
| 6,957,107 | B2 | 10/2005 | Rogers et al. |
| 7,044,911 | B2 | 5/2006 | Drinan et al. |
| 7,051,120 | B2 | 5/2006 | Greene et al. |
| 7,285,090 | B2 | 10/2007 | Stivoric et al. |
| 7,311,665 | B2 | 12/2007 | Hawthorne et al. |
| 7,462,149 | B2 | 12/2008 | Hawthorne et al. |
| 7,611,461 | B2 | 11/2009 | Hawthorne et al. |
| 7,641,611 | B2 | 1/2010 | Hawthorne et al. |
| 2002/0156650 | A1 | 10/2002 | Klein et al. |
| 2003/0114735 | A1 | 6/2003 | Silver et al. |
| 2003/0126593 | A1 | 7/2003 | Mault |
| 2003/0172940 | A1 | 9/2003 | Rogers et al. |
| 2004/0019503 | A1 | 1/2004 | Berenguer |
| 2004/0122486 | A1 | 6/2004 | Stahmann et al. |
| 2005/0177615 | A1 | 8/2005 | Hawthorne et al. .......... 709/200 |
| 2007/0100666 | A1 | 5/2007 | Stivoric et al. |

OTHER PUBLICATIONS

Rene T. Towa, Office Action, May 22, 2012, U.S. Appl. No. 11/441,694, Titled "Method and Apparatus for Remote Blood Alcohol Monitoring", filed Apr. 25, 2006, 24 pages.
Rene T. Towa, Office Action, Oct. 30, 2008, U.S. Appl. No. 11/411,686 Titled "Method and Apparatus for Remote Blood Alcohol Monitoring", filed Apr. 25, 2006.
Rene T. Towa, Office Action, Jan. 9, 2009, U.S. Appl. No. 11/411,692 Titled "Method and Apparatus for Remote Blood Alcohol Monitoring", filed Apr. 25, 2006.
Rene T. Towa, Office Action, Apr. 16, 2009, U.S. Appl. No. 11/411,692 Titled "Method and Apparatus for Remote Blood Alcohol Monitoring", filed Apr. 25, 2006.
U.S. Appl. No. 11/441,694, filed Apr. 25, 2006, Non-Final Office Action Mail Date Nov. 29, 2011, Rene T. Towa, 18 pages.
U.S. Appl. No. 10/441,960, filed May 19, 2003, (U.S. Pat. No. 7,311,665, Issued Dec. 25, 2007) Non-Final Office Action dated Oct. 4, 2004, 9 pages.
U.S. Appl. No. 10/441,960, filed May 19, 2003, (U.S. Pat. No. 7,311,665, Issued Dec. 25, 2007) Non-Final Office Action dated Jun. 30, 2005, 9 pages.
U.S. Appl. No. 10/441,960, filed May 19, 2003, (U.S. Pat. No. 7,311,665, Issued Dec. 25, 2007) Final Office Action dated Jan. 24, 2006, 10 pages.
U.S. Appl. No. 10/441,960, filed May 19, 2003, (U.S. Pat. No. 7,311,665, Issued Dec. 25, 2007) Non-Final Office Action dated Sep. 11, 2006, 7 pages.
U.S. Appl. No. 10/441,960, filed May 19, 2003, (U.S. Pat. No. 7,311,665, Issued Dec. 25, 2007) Notice of Allowance dated Apr. 23, 2007, 6 pages.
U.S. Appl. No. 10/441,960, filed May 19, 2003, (U.S. Pat. No. 7,311,665, Issued Dec. 25, 2007) Notice of Allowance dated Aug. 9, 2007, 5 pages.
U.S. Appl. No. 10/441,960, filed May 19, 2003, (U.S. Pat. No. 7,311,665, Issued Dec. 25, 2007) Notice of Allowance dated Oct. 1, 2007, 2 pages.
U.S. Appl. No. 11/104,810, filed Apr. 13, 2005, Non-final Office Action dated Jul. 13, 2009, 13 pages.
U.S. Appl. No. 10/441,940, filed May 19, 2003, (U.S. Pat. No. 7,462,149, Issued Dec. 9, 2008) Non-Final Office Action dated Jul. 11, 2006, 18 pages.
U.S. Appl. No. 10/441,940, filed May 19, 2003, (U.S. Pat. No. 7,462,149, Issued Dec. 9, 2008) Final Office Action dated Nov. 29 , 2006, 18 pages.
U.S. Appl. No. 10/441,940, filed May 19, 2003, (U.S. Pat. No. 7,462, 149, Issued Dec. 9, 2008) Advisory Action dated Jan. 30, 2007, 4 pages.
U.S. Appl. No. 10/441,940, filed May 19, 2003, (U.S. Pat. No. 7,462,149, Issued Dec. 9, 2008) Non-Final Office Action dated May 10, 2007, 30 pages.
U.S. Appl. No. 10/441,940, filed May 19, 2003, (U.S. Pat. No. 7,462,149, Issued Dec. 9, 2008) Non-Final Office Action dated Dec. 28, 2007, 19 pages.
U.S. Appl. No. 10/441,940, filed May 19, 2003, (U.S. Pat. No. 7,462,149, Issued Dec. 9, 2008) Notice of Allowance dated Oct. 8, 2008, 7 pages.
U.S. Appl. No. 11/411,692, filed Apr. 25, 2006, (U.S. Pat. No. 7,611,461, Issued Nov. 3, 2009) Notice of Allowance dated Jul. 17, 2009, 9 pages.
U.S. Appl. No. 11/411,686, filed Apr. 25, 2006, (U.S. Pat. No. 7,641,611, Issued Jan. 5, 2010) Final Office Action dated Apr. 16, 2009, 10 pages.
U.S. Appl. No. 11/411,686, filed Apr. 25, 2006 (U.S. Pat. No. 7,641,611, Issued Jan. 5, 2010) Advisory Action dated Jun. 26, 2009, 4 pages.
U.S. Appl. No. 11/411,686, filed Apr. 25, 2006 (U.S. Pat. No. 7,641,611, Issued Jan. 5, 2010) Notice of Allowance dated Oct. 20, 2009, 8 pages.
U.S. Appl. No. 11/104,810, filed Apr. 13, 2005, Final Office Action Dated Mar. 2, 2010, 15 pages.
Michael C. Astorino, Interview Summary, Jan. 3, 2007, U.S. Appl. No. 10/441,960 Titled "Bio-Information Sensor Monitoring System and Method", filed May 19, 2003, 3 pages.
"Medtronic Begins Worldwide Rollout of Innovative Medtronic CareLink Programmer to Enhance Cardiac Care," Business Wire, Mar. 18, 2002, Business Wire HealthWire, Minneapolis, 3 pages.
"Medtronic CareLink Network Extends Cardiac Patient Monitoring Beyond Clinic Walls," Virtual Medical Worlds, Monthly Newsletter, Mar. 18, 2002, Atlanta, 3 pages.
"Medtronic Completes Phase One of Its Medtronic CareLink Patient Management Network Rollout; American College of Cardiology Meeting 2002," Mar. 18, 2002, Business Wire, Inc., Minneapolis, 2 pages.
Kristine K. Rapillo, Office Action, Dec. 120, 2010 U.S. Appl. No. 11/104,810 Titled "Bio-Information Sensor Monitoring System and Method", filed Apr. 13, 2005, 19 pages.
Rene T. Towa, Office Action, Jan. 6, 2011, U.S. Appl. No. 11/411,694 Titled "Method and Apparatus for Remote Blood Alcohol Monitoring", filed Apr. 25, 2006, 17 pages.

(56) References Cited

OTHER PUBLICATIONS

Kristine K. Rapillo, Office Action, Jun. 28, 2011, U.S. Appl. No. 11/104,810 Titled "Bio-Information Sensor Monitoring System and Method", filed Mar. 221, 2005, 14 pages.
*Alcohol Monitoring Systems, Inc. v. BI Inc.*, No. 11-cv-00301-DME-CBS, Complaint, Doc. #1 (D. Colo. Feb. 4, 2011), 90 pages.
*Alcohol Monitoring Systems, Inc. v. BI Inc.*, No. 11-cv-00301-DME-CBS, Answer, Doc. #10 (D. Colo. Mar. 21, 2011), 33 pages.
*Alcohol Monitoring Systems, Inc. v. BI Inc.*, No. 11-cv-00301-DME-CBS, Answer to Counterclaim and Counterclaim, Doc. #11 (D. Colo. Apr. 11, 2011), 8 pages.
*Alcohol Monitoring Systems, Inc. v. BI Inc.*, No. 11-cv-00301-DME-CBS, Motion for Stay, Doc. #17 (D. Colo. Apr. 27, 2011), 194 pages.
*Alcohol Monitoring Systems, Inc. v. BI Inc.*, No. 11-cv-00301-DME-CBS, Motion to Dismiss, Doc. #21 (D. Colo. May 2, 2011), 5 pages.
*Alcohol Monitoring Systems, Inc. v. BI Inc.*, No. 11-cv-00301-DME-CBS, Answer to Counterclaims, Doc. #22 (D. Colo. May 2, 2011), 6 pages.
*Alcohol Monitoring Systems, Inc. v. BI Inc.*, No. 11-cv-00301-DME-CBS, Opposition to Motion for Stay, Doc. #26 (D. Colo. May 18, 2011), 29 pages.
*Alcohol Monitoring Systems, Inc. v. BI Inc.*, No. 11-cv-00301-DME-CBS, Order Denying Stay, Doc. #27 (D. Colo. May 19, 2011),2 pages.
*Alcohol Monitoring Systems, Inc. v. BI Inc.*, No. 11-cv-00301-DME-CBS, Renewed Motion for Stay, Doc. #32 (D. Colo. May 27, 2011), 74 pages.
*Alcohol Monitoring Systems, Inc. v. BI Inc.*, No. 11-cv-00301-DME-CBS, Motion for Leave to File 1st Amended Complaint, Doc. #38 (D. Colo. Jun. 10, 2011),169 pages.
*Alcohol Monitoring Systems, Inc. v. BI Inc.*, No. 11-cv-00301-DME-CBS, Opposition to Renewed Motion for Stay, Doc. #41 (D. Colo. Jun. 17, 2011),14 pages.
*Alcohol Monitoring Systems, Inc. v. BI Inc.*, No. 11-cv-00301-DME-CBS, Order Denying Renewed Motion for Stay, Doc. #42 (D. Colo. Jun. 24, 2011), 2 pages.
Request for Inter Partes Reexamination, Filed Apr. 21, 2011, U.S. Pat. No. 7,462,149 Titled "Method and Apparatus For Remote Blood Alcohol Monitoring," Issued on Dec. 9, 2008 U.S. Appl. No. 10/441,940, filed May 19, 2003, 83 pages.
Order Granting Request for Inter Partes Reexamination, Mailed on May 20, 2011, U.S. Appl. No. 95/001,609 Titled "Method and Apparatus for Remote Blood Alcohol Monitoring,", filed Apr. 21, 2011, 12 pages.
Jeffrey L. Gellner, Office Action, May 20, 2011, U.S. Appl. No. 95/001,609 Titled "Method and Apparatus for Remote Blood Alcohol Monitoring,", filed Apr. 21, 2011, 39 pages.
Repsonse to Office Action, Filed Jul. 20, 2011, U.S. Appl. No. 95/001,609, filed Apr. 21, 2011, 39 pages.
Information Disclosure Statement, Filed Jul. 20, 2011, U.S. Appl. No. 95/001,609, filed Apr. 21, 2011, 10 pages.
U.S. Appl. No. 11/441,694, filed Apr. 25, 2006, Non-Final Office Action dated Apr. 22, 2011, Rene T. Towa. 17 pages.
U.S. Appl. No. 11/411,694, filed Apr. 25, 2006, Non-Final Office Action dated Aug. 31, 2010, Rene T. Towa, 19 pages.
Rene T. Towa, Notice of Allowance, Aug. 15, 2012, U.S. Appl. No. 11/411,694, Titled "Method and Apparatus for Remote Blood Alcohol Monitoring", filed Apr. 25, 2006, 7 pages.
Official Action for U.S. Appl. No. 11/104,810, mailed Aug. 17, 2012 15 pages.
Litigation Search Report for U.S. Appl. No. 95/001,609, filed Aug. 29, 2011, 51 pages.
Petition Under 37 C.F.R. §§ 1.181(a)(3), 1.182, & 1.183 and Brief in Support of Same, U.S. Appl. No. 95/001,609, filed Sep. 8, 2011, 6 pages.
Petition Under 37 C.F.R. §§ 1.181(a)(3), 1.182, & 1.183 and Brief in Support of Same Including Response to Patent Owner's Petition to Expunge, U.S. Appl. No. 95/001,609, filed Sep. 23, 2011, 10 pages.
Decision Dismissing Petitions, U.S. Appl. No. 95/001,609, mailed Nov. 15, 2011, 4 pages.
Reexamination—Patent Owner Power of Attorney and Statement under 37 CFR 3.73(b), U.S. Appl. No. 95/001,609, filed Nov. 21, 2011, 2 pages.
Petition Under 37 C.F.R. § 1.183 and Brief in Support of Same, U.S. Appl. No. 95/001,609, filed Nov. 22, 2011, 13 pages.
Third Party Requester's Response in Opposition to Patent Owner's Petition Under 37 C.F.R. § 1.183, U.S. Appl. No. 95/001,609, filed Dec. 12, 2011, 19 pages.
Third Party Requester's Reply to the Patent Owner's Response under 35 USC §314(b)(2), U.S. Appl. No. 95/001,609, filed Dec. 13, 2011, 46 pages.
Petition Under 37 C.F.R. §§ 1.181 and Brief in Support of Same, U.S. Appl. No. 95/001,609, filed Dec. 21, 2011, 11 pages.
Third Party Requester's Response in Opposition to Patent Owner's Petition Under 37 CFR. § 1.181, U.S. Appl. No. 95/001,609, filed Jan. 5, 2012, 5 pages.
Decision Dismissing Petitions as Moot, U.S. Appl. No. 95/001,609, mailed Jan. 10, 2012, 3 pages.
Litigation Search Report for U.S. Appl. No. 95/001,609, filed Jan. 11, 2012, 46 pages.
Decision Dismissing Petitions, U.S. Appl. No. 95/001,609, mailed Feb. 21, 2012, 3 pages.
Official Action for U.S. Appl. No. 95/001,609, mailed Feb. 21, 2012, 100 pages.
Response to Office Action, U.S. Appl. No. 95/001,609, filed Apr. 20, 2012, 48 pages.
Petition Under 37 C.F.R. §§ 1.181 and Brief in Support of Same, U.S. Appl. No. 95/001,609, filed Apr. 20, 2012, 7 pages.
Third Party Requester's Reply to the Patent Owner's Response under 35 USC §314(b)(2), U.S. Appl. No. 95/001,609, filed May 7, 2012, 16 pages.
Decision on Petition under 37 CFR 1.181, U.S. Appl. No. 95/001,609, mailed Jun. 25, 2012, 5 pages.
Request for Reconsideration of Apr. 20, 2012 Petition Under 37 C.F.R. §§ 1.181 and Brief in Support of Same, U.S. Appl. No. 95/001,609, filed Jul. 3, 2012, 6 pages.
Decision on Petition under 37 CFR 1.181, U.S. Appl. No. 95/001,609, mailed Aug. 15, 2012, 6 pages.
Petition to Review Decision of Technology Center Director and Brief in Support of Same, U.S. Appl. No. 95/001,609, filed Aug. 21, 2012, 6 pages.
Decision on Petition Requesting Review of CRU Director, U.S. Appl. No. 95/001,609, mailed May 14, 2013, 15 pages.
Litigation Search Report for U.S. Appl. No. 95/001,609, filed May 23, 2013, 47 pages.
Official Action for U.S. Appl. No. 95/001,609, mailed Jun. 20, 2013, 95 pages.
Response to Office Action, U.S. Appl. No. 95/001,609, filed Aug. 20, 2013, 51 pages.
Third Party Requester's Reply to the Patent Owner's Response under 35 USC §314(b)(2), U.S. Appl. No. 95/001,609, filed Sep. 19, 2013, 35 pages.
Official Action for U.S. Appl. No. 95/001,609, mailed Dec. 13, 2013, 12 pages.
Amendment and Notice Under MPEP 2686, U.S. Appl. No. 95/001,609, filed Dec. 23, 2013, 4 pages.
Third Party Requester's Reply to the Patent Owner's Response under 35 USC §314(b)(2), U.S. Appl. No. 95/001,609, filed Jan. 23, 2014, 19 pages.
Official Action for U.S. Appl. No. 95/001,609, mailed Apr. 1, 2014, 8 pages.
Statement under 37 CFR §1.98(a0(2)(iv), U.S. Appl. No. 95/001,609, filed May 13, 2014, 5 pages.
Third Party Requester's Reply to the Patent Owner's Response under 37 CFR §1.951(b), U.S. Appl. No. 95/001,609, filed May 22, 2014, 94 pages.

(56) References Cited

OTHER PUBLICATIONS

Official Action for U.S. Appl. No. 95/001,609, mailed Jun. 4, 2014, 10 pages.
Notice of Appeal by Third Party Requester in Inter Partes Reexam, U.S. Appl. No. 95/001,609, filed Jun. 25, 2014, 4 pages.
Petition Under 37 C.F.R. § 1.181 and Brief in Support of Same, U.S. Appl. No. 95/001,609, filed Jul. 24, 2014, 10 pages.
Third Party Requester's Response in Opposition to Patent Owner's Petition Under 37 CFR. § 1.181, U.S. Appl. No. 95/001,609, filed Aug. 18, 2014, 27 pages.
Appeal Brief in Support of Appellant/Third-Party Requester's Appeal to the Patent Trial and Appeal Board, U.S. Appl. No. 95/001,609, filed Aug. 18, 2014, 367 pages.
Inter Partes Reexamination Notification re Brief for U.S. Appl. No. 95/001,609, mailed Sep. 9, 2014, 12 pages.
Certificate of Word Count Pursuant to 37 C.F.R. § 1.943, U.S. Appl. No. 95/001,609, filed Sep. 12, 2014, 1 page.
Supplement to Petition Filed Under 37 C.F.R. § 1.181, U.S. Appl. No. 95/001,609, filed Sep. 25, 2014, 15 pages.
Decision Dismissing Petition to Terminate Inter Partes Reexamination Proceeding, U.S. Appl. No. 95/001,609, mailed Oct. 1, 2014, 13 pages.
Renewed Petition to Terminate Proceeding, with Contingent Motion to Amend, U.S. Appl. No. 95/001,609, filed Oct. 8, 2014, 9 pages.
Respondent Brief, U.S. Appl. No. 95/001,609, filed Oct. 14, 2014, 19 pages.
Third Party Requester's Response in Opposition to Patent Owner's Renewed Petition to Terminate Proceeding, U.S. Appl. No. 95/001,609, filed Nov. 11, 2014, 108 pages.
Supplement to Oct. 8, 2014 Renewed Petition, U.S. Appl. No. 95/001,609, filed Nov. 7, 2014, 36 pages.
Third Party Requester's Response to Patent Owner's Supplement to Oct. 8, 2014 Renewed Petition, U.S. Appl. No. 95/001,609, filed Dec. 5, 2014, 2 pages.
Amendment, U.S. Appl. No. 95/001,609, filed Feb. 5, 2015, 3 pages.
Second Supplement to Oct. 8, 2014 Renewed Petition, U.S. Appl. No. 95/001,609, filed Feb. 5, 2015, 2 pages.
Decision Granting Petition to Terminate Inter partes Reexamination Proceeding, U.S. Appl. No. 95/001,609, mailed Feb. 6, 2015, 11 pages.
Request for Inter Partes Reexamination of U.S. Pat. No. 7,641,611 entitled "Method and Apparatus for Remote Blood Alcohol Monitoring", Apr. 21, 2011, 99 pages.
Litigation Search Report for U.S. Appl. No. 95/001,610, filed Apr. 29, 2011, 16 pages.
Order Granting Request for Inter Partes Reexamination, U.S. Appl. No. 95/001,610, mailed May 20, 2011, 12 pages.
Official Action for U.S. Appl. No. 95/001,610, mailed May 20, 2011, 16 pages.
Response, U.S. Appl. No. 95/001,610, filed Jul. 20, 2011, 20 pages.
Reexamination—Patent Owner Power of Attorney and Statement under 37 CFR 3.73(b), U.S. Appl. No. 95/001,610, filed Jul. 20, 2011, 2 pages.
Third Party Requester's Reply to the Patent Owner's Response Under 35 USC §314(b)(2), U.S. Appl. No. 95/001,610, filed Aug. 18, 2011, 29 pages.
Litigation Search Report for U.S. Appl. No. 95/001,610, filed Aug. 26, 2011, 15 pages.
Official Action for U.S. Appl. No. 95/001,610, mailed Sep. 30, 2011, 42 pages.
Petition Under 37 C.F.R. §1.182—Questions Not Specifically Provided for, U.S. Appl. No. 95/001,610, filed Oct. 31, 2011, 40 pages.
Petition Under 37 C.F.R. §1.181 to Reopen Prosecution and Enter Supplemental Response, U.S. Appl. No. 95/001,610, filed Oct. 31, 2011, 45 pages.
Reexamination—Patent Owner Power of Attorney or Revocation of Power of Attorney with a New Power of Attorney and Change of Correspondence Address, and Statement under 37 CFR 3.73(b), U.S. Appl. No. 95/001,610, filed Nov. 21, 2011, 2 pages.
Litigation Search Report for U.S. Appl. No. 95/001,610, filed Jan. 6, 2012, 63 pages.
Decision on Petition for Reopening Prosecution under 37 C.F.R. §1.181, U.S. Appl. No. 95/001,610, mailed Jan. 10, 2012, 3 pages.
Litigation Search Report for U.S. Appl. No. 95/001,610, filed Jan. 11, 2012, 65 pages.
Official Action for U.S. Appl. No. 95/001,610, mailed Jan. 13, 2012, 45 pages.
Decision Dismissing Petition as Moot, U.S. Appl. No. 95/001,610, mailed Jan. 17, 2012, 3 pages.
Response to Jan. 13, 2012 Office Action, U.S. Appl. No. 95/001,610, filed Mar. 13, 2012, 53 pages.
Third Party Requester's Reply to the Patent Owner's Response Under 35 USC §314(b)(2), U.S. Appl. No. 95/001,610, filed Apr. 13, 2012, 14 pages.
Litigation Search Report for U.S. Appl. No. 95/001,610, filed Apr. 26, 2012, 26 pages.
Official Action for U.S. Appl. No. 95/001,610, mailed May 23, 2012, 110 pages.
Response to May 23, 2012 Office Action, U.S. Appl. No. 95/001,610, filed Jul. 23, 2012, 44 pages.
Third Party Requester's Reply to the Patent Owner's Response Under 35 USC §314(b)(2), U.S. Appl. No. 95/001,610, filed Aug. 23, 2012, 9 pages.
Litigation Search Report for U.S. Appl. No. 95/001,610, filed Sep. 20, 2012, 29 pages.
Official Action for U.S. Appl. No. 95/001,610, mailed Oct. 26, 2012, 37 pages.
Official Action for U.S. Appl. No. 95/001,610, mailed Jan. 23, 2013, 38 pages.
Notice of Appeal by Third Party Requester in Inter Partes Reexam, U.S. Appl. No. 95/001,610, filed Feb. 22, 2013, 5 pages.
Appeal Brief in Support of Appellant/Third-Party Requester's Appeal to the Patent Trial and Appeal Board, U.S. Appl. No. 95/001,610, filed Apr. 22, 2013, 265 pages.
Inter Partes Reexamination Notification re Brief for U.S. Appl. No. 95/001,610, mailed Apr. 26, 2013, 4 pages.
Certificate of Word Count Pursuant to 37 C.F.R. § 1.943, U.S. Appl. No. 95/001,610, filed May 15, 2013, 1 page.
Inter Partes Reexamination Notification re Brief for U.S. Appl. No. 95/001,610, mailed May 29, 2013, 6 pages.
Respondent Brief, U.S. Appl. No. 95/001,610, filed Jun. 14, 2013, 584 pages. (Uploaded in 2 parts).
Appeal Brief in Support of Appellant/Third-Party Requester's Appeal to the Patent Trial and Appeal Board, U.S. Appl. No. 95/001,610, filed Jul. 1, 2013, 256 pages.
Clarification of the Record, U.S. Appl. No. 95/001,610, mailed Jul. 31, 2013, 4 pages.
Amended Respondent Brief, U.S. Appl. No. 95/001,610, filed Jul. 1, 2013, 587 pages. (Uploaded in 2 parts).
Official Action for U.S. Appl. No. 95/001,610, mailed Sep. 11, 2013, 3 pages.
Appeal Docketing Notice for U.S. Appl. No. 95/001,610, mailed Sep. 24, 2013, 3 pages.
Decision on Appeal for U.S. Patent Appeal No. 2013-010790, U.S. Appl. No. 95/001,610, mailed Mar. 31, 2014, 17 pages.
Litigation Search Report for U.S. Appl. No. 95/001,610, filed Aug. 14, 2014, 37 pages.
Notice of Intent to Issue Inter Partes Reexamination Certificate for U.S. Appl. No. 95/001,610, mailed Aug. 18, 2014, 5 pages.
*Alcohol Monitoring Systems, Inc. v. BI Inc.*, No. 11-cv-00301-DME. CBS, Notice of Entry of Appearance, Doc. #2 (D. Colo. Feb. 4, 2011), 2 pages.
*Alcohol Monitoring Systems, Inc. v. BI Inc.*, No. 11-cv-00301-DME. CBS, Report on the Filing or Determination of an Action Regarding a Patent or Trademark, Doc. #3, (D. Colo. Feb. 8, 2011), 1 page.
*Alcohol Monitoring Systems, Inc. v. BI Inc.*, No. 11-cv-00301-DME. CBS, Order of Reference to United States Magistrate, Doc. #4 (D. Colo. Feb. 8, 2011), 2 pages.
*Alcohol Monitoring Systems, Inc. v. BI Inc.*, No. 11-cv-00301-DME. CBS, Order Setting Rule 16(b) Scheduling Conference and Rule 26(f) Planning Meeting, Doc. #5 (D. Colo. Feb. 10, 2011), 4 pages.

(56) References Cited

OTHER PUBLICATIONS

*Alcohol Monitoring Systems, Inc.* v. *BI Inc.*, No. 11-cv-00301-DME-CBS, Summons in a Civil Action (Executed and Returned), Doc. #6 (D. Colo. Feb. 11, 2011), 2 pages.
*Alcohol Monitoring Systems, Inc.* v. *BI Inc.*, No. 11-cv-00301-DME-CBS, Stipulation for Extension of Time to Respond to Complaint, Doc. #7 (D. Colo. Feb. 25, 2011), 3 pages.
*Alcohol Monitoring Systems, Inc.* v. *BI Inc.*, No. 11-cv-00301-DME-CBS, Corporate Disclosure Statement, Doc. #9 (D. Colo. Mar. 1, 2011), 2 pages.
*Alcohol Monitoring Systems, Inc.* v. *BI Inc.*, No. 11-cv-00301-DME-CBS, Minute Order, Doc. #12 (D. Colo. Apr. 12, 2011), 1 page.
*Alcohol Monitoring Systems, Inc.* v. *BI Inc.*, No. 11-cv-00301-DME-CBS, Notice of Entry of Appearance, Doc. #13 (D. Colo. Apr. 12, 2011), 2 pages.
*Alcohol Monitoring Systems, Inc.* v. *BI Inc.*, No. 11-cv-00301-DME-CBS, Notice of Entry of Appearance, Doc. #14 (D. Colo. Apr. 13, 2011), 2 pages.
*Alcohol Monitoring Systems, Inc.* v. *BI Inc.*, No. 11-cv-00301-DME-CBS, Proposed Scheduling Order, Doc. #15 (D. Colo. Apr. 18, 2011), 12 pages.
*Alcohol Monitoring Systems, Inc.* v. *BI Inc.*, No. 11-cv-00301-DME-CBS, Courtroom Minutes/Minute Order, Doc. #16 (D. Colo. Apr. 25, 2011), 1 page.
*Alcohol Monitoring Systems, Inc.* v. *BI Inc.*, No. 11-cv-00301-DME-CBS, Minute Order, Doc. #19 (D. Colo. Apr. 29, 2011), 1 page.
*Alcohol Monitoring Systems, Inc.* v. *BI Inc.*, No. 11-cv-00301-DME-CBS, Notice of Entry of Appearance, Doc. #20 (D. Colo. Apr. 29, 2011), 2 pages.
*Alcohol Monitoring Systems, Inc.* v. *BI Inc.*, No. 11-cv-00301-DME-CBS, Revised Proposed Scheduling Order, Doc. #23 (D. Colo. May 13, 2011 ), 14 pages.
*Alcohol Monitoring Systems, Inc.* v. *BI Inc.* No. 11-cv-00301-DME-CBS, Joint Motion for Entry of Stipulated Protective Order, Doc. #24 (D. Colo. May 13, 2011 ), 24 pages.
*Alcohol Monitoring Systems, Inc.* v. *BI Inc.*, No. 11-cv-00301-DME-CBS, Scheduling Order, Doc. #28 (D. Colo. May 19, 2011), 15 pages.
*Alcohol Monitoring Systems, Inc.* v. *BI Inc.*, No. 11-cv-00301-DME-CBS, Response to Motion to Dismiss Affirmative Defense of Inequitable Conduct, Doc. #29 (D. Colo. May 23, 2011), 35 pages.
*Alcohol Monitoring Systems, Inc.* v. *BI Inc.*, No. 11-cv-00301-DME-CBS, Minute Order, Doc. #30 (D. Colo. May 23, 2011), 1 page.
*Alcohol Monitoring Systems, Inc.* v. *BI Inc.*, No. 11-cv-00301-DME-CBS, Stipulated Protective Order, Doc. #31 (D. Colo. May 23, 2011), 22 pages.
*Alcohol Monitoring Systems, Inc.* v. *BI Inc.*, No. 11-cv-00301-DME-CBS, Stipulation to Dismiss Inequitable Conduct, Doc. #34 (D. Colo. May 27, 2011 ), 3 pages.
*Alcohol Monitoring Systems, Inc.* v. *BI Inc.*, No. 11-cv-00301-DME-CBS, Motion to Set Markman Hearing, Doc. #36 (D. Colo. Jun. 6, 2011 ), 5 pages.
*Alcohol Monitoring Systems, Inc.* v. *BI Inc.*, No. 11-cv-00301-DME-CBS, Partial Transcript of Rule 16(b) Scheduling Conference, Doc.#41 (D. Colo. Jun. 15, 2011), 30 pages.
*Alcohol Monitoring Systems, Inc.* v. *BI Inc.*, No. 11-cv-00301-DME-CBS, Transcript of Rule 16(b) Scheduling Conference, Doc. #43 (D. Colo. Jun. 28, 2011), 42 pages.
*Alcohol Monitoring Systems, Inc.* v. *BI Inc.*, No. 11-cv-00301-DME-CBS, Order Re BI Incorporated's Motion to Dismiss Alcohol Monitoring Systems, Inc.'s Affimative Defense of Inequitable Conduct, (Doc.21), Doc.#44 (D. Colo. Jul. 1, 2011), 1 page.
*Alcohol Monitoring Systems, Inc.* v. *BI Inc.*, No. 11-cv-00301-DME-CBS, Motion to Set Markman Hearing on Honorable Judge David Ebel's Calendar, Doc. #45 (D. Colo. Jul. 5, 2011 ), 5 pages.
*Alcohol Monitoring Systems, Inc.* v. *BI Inc.*, No. 11-cv-00301-DME-CBS, Defendant BI Incorporated's Opposition to Plaintiff Alcohol Monitoring Systems, Inc.'s Motion for Leave to File First Amended Complaint, Doc. #46 (D. Colo. Jul. 5, 2011 ), 67 pages.
*Alcohol Monitoring Systems, Inc.* v. *BI Inc.*, No. 11-cv-00301-DME-CBS, Alcohol Monitoring System's First Amended Answer to BI Incorporated's Counterclaim for Infringement, and Counterclaim, Doc. #47 (D. Colo. Jul. 7, 2011 ), 8 pages.
*Alcohol Monitoring Systems, Inc.* v. *BI Inc.*, No. 11-cv-00301-DME-CBS, Transcript of Motion Hearing, Doc.#48 (D. Colo. Jul. 8, 2011), 44 pages.
*Alcohol Monitoring Systems, Inc.* v. *BI Inc.*, No. 11-cv-00301-DME-CBS, Plaintiff's Reply in Support of Motion for Leave to File First Amended Complaint, Doc.#49 (D. Colo. Jul. 15, 2011), 20 pages.
*Alcohol Monitoring Systems, Inc.* v. *BI Inc.*, No. 11-cv-00301-DME-CBS, Defendant BI Incorporated's Opposition to Plaintiff Alcohol Monitoring Systems, Inc's Motion to Set Markman Hearing, Doc.#50 (D. Colo. Jul. 29, 2011), 26 pages.
*Alcohol Monitoring Systems, Inc.* v. *BI Inc.*, No. 11-cv-00301-DME-CBS, Joint Chart of Disputed Patent Terms for Construction, Doc.#51 (D. Colo. Aug. 1, 2011), 43 pages.
*Alcohol Monitoring Systems, Inc.* v. *BI Inc.*, No. 11-cv-00301-DME-CBS, Order Re: Motion to Set Markman Hearing on Honorable Judge David Ebel's Calendar, Doc.#52 (D. Colo. Aug. 8, 2011), 1 page.
*Alcohol Monitoring Systems, Inc.* v. *BI Inc.*, No. 11-cv-00301-DME-CBS, Stipulated Motion to Modify Scheduling Order, Doc. #53 (D. Colo. Oct. 7, 2011), 2 pages.
*Alcohol Monitoring Systems, Inc.* v. *BI Inc.*, No. 11-cv-00301-DME-CBS, Stipulation of Dismissal of AMS's Third Claim for Relief, Doc.#55 (D. Colo. Oct. 10, 2011), 2 pages.
*Alcohol Monitoring Systems, Inc.* v. *BI Inc.*, No. 11-cv-00301-DME-CBS, Joint Motion for Extension of Time to File Claim Construction Briefs, Doc.#57 (D. Colo. Oct. 28, 2011), 4 pages.
*Alcohol Monitoring Systems, Inc.* v. *BI Inc.*, No. 11-cv-00301-DME-CBS, Joint Motion to Exceed Page Limitation, Doc.#60 (D. Colo. Nov. 4, 2011), 3 pages.
*Alcohol Monitoring Systems, Inc.* v. *BI Inc.*, No. 11-cv-00301-DME-CBS, Alcohol Monitoring Systems Inc's Motion for Summary Judgement of Non-Infringement regarding the '884 Patent, Doc.#61 (D. Colo. Nov. 4, 2011), 50 pages.
*Alcohol Monitoring Systems, Inc.* v. *BI Inc.*, No. 11-cv-00301-DME-CBS, Claim Construction Brief by Alcohol Monitoring Systems, Inc., Doc.#62 (D. Colo. Nov. 4, 2011), 182 pages (Uploaded in 2 parts).
*Alcohol Monitoring Systems, Inc.* v. *BI Inc.*, No. 11-cv-00301-DME-CBS, BI's Opening Claim Construction Brief, Doc.#63 (D. Colo. Nov. 4, 2011), 1896 pages. (Uploaded in 13 parts).
*Alcohol Monitoring Systems, Inc.* v. *BI Inc.*, No. 11-cv-00301-DME-CBS, Notice of Entry of Appearance, Doc.#64 (D. Colo. Nov. 4, 2011), 2 pages.
*Alcohol Monitoring Systems, Inc.* v. *BI Inc.*, No. 11-cv-00301-DME-CBS, Order Granting Joint Motion to Exceed Page Limit, Doc.#65 (D. Colo. Nov. 4, 2011), 1 page.
*Alcohol Monitoring Systems, Inc.* v. *BI Inc.*, No. 11-cv-00301-DME-CBS, BI's Motion to Continue Markman Hearing Pending Reexamination of U.S. Pat. Nos. 7,462,149 and 7,641,611, Doc.#66 (D. Colo. Nov. 14, 2011), 123 pages.
*Alcohol Monitoring Systems, Inc.* v. *BI Inc.*, No. 11-cv-00301-DME-CBS, Joint Motion to Exceed Page Limitation for Claim Construction Response Briefs, Doc.#67 (D. Colo. Nov. 28, 2011), 4 pages.
*Alcohol Monitoring Systems, Inc.* v. *BI Inc.*, No. 11-cv-00301-DME-CBS, Defendant BI's Response in Opposition to Alcohol Monitoring Systems, Inc.'s Motion for Summary Judgment of Non-Infringement Regarding the '884 Patent, Doc.#68 (D. Colo. Nov. 28, 2011), 39 pages.
*Alcohol Monitoring Systems, Inc.* v. *BI Inc.*, No. 11-cv-00301-DME-CBS, Defendant BI's Rebuttal Claim Construction Brief, Doc.#69 (D. Colo. Nov. 28, 2011), 31 pages.
*Alcohol Monitoring Systems, Inc.* v. *BI Inc.*, No. 11-cv-00301-DME-CBS, Plaintiff Alcohol Monitoring Systems, Inc.'s Claim Construction Response Brief, Doc.#70 (D. Colo. Nov. 28, 2011), 72 pages.

(56) References Cited

OTHER PUBLICATIONS

*Alcohol Monitoring Systems, Inc. v. BI Inc.*, No. 11-cv-00301-DME-CBS, Order Granting BI's Motion to Continue Markman Hearing Pending Reexamination of U.S. Pat. Nos. 7,462,149 and 7,641,611 and Order Scheduling Status Conference, Doc.#71 (D. Colo. Nov. 28, 2011), 2 pages.

*Alcohol Monitoring Systems, Inc. v. BI Inc.*, No. 11-cv-00301-DME-CBS, Alcohol Monitoring System's, Inc.'s Status Report to Magistrate Judge Craig Shaffer Pursuant to Section XI of the Scheduling Order, Doc.#72 (D. Colo. Dec. 1, 2011), 4 pages.

*Alcohol Monitoring Systems, Inc. v. BI Inc.*, No. 11-cv-00301-DME-CBS, BI's Status Report to Magistrate Judge Shaffer, Doc. #73 (D. Colo. Dec. 1, 2011), 4 pages.

*Alcohol Monitoring Systems, Inc. v. BI Inc.*, No. 11-cv-00301-DME-CBS, Notice of Filing of Exhibit 1 to Alcohol Monitoring System's, Inc.'s Status Report to Magistrate Judge Craig Shaffer Pursuant to Section XI of the Scheduling Order, Doc.#74 (D. Colo. Dec. 2, 2011), 43 pages.

*Alcohol Monitoring Systems, Inc. v. BI Inc.*, No. 11-cv-00301-DME-CBS, Alcohol Monitoring Systems, Inc.'s Status Report, Doc.#75 (D. Colo. Dec. 6, 2011), 11 pages.

*Alcohol Monitoring Systems, Inc. v. BI Inc.*, No. 11-cv-00301-DME-CBS, BI's Response to AMS' Status Report, Doc.#76 (D. Colo. Dec. 6, 2011), 22 pages.

*Alcohol Monitoring Systems, Inc. v. BI Inc.*, No. 11-cv-00301-DME-CBS, Minute Entry for Satus Conference, Doc.#77 (D. Colo. Dec. 9, 2011), 2 pages.

*Alcohol Monitoring Systems, Inc. v. BI Inc.*, No. 11-cv-00301-DME-CBS, First Amended Complaint and Jury Demand, Doc.#78 (D. Colo. Dec. 9, 2011), 141 pages.

*Alcohol Monitoring Systems, Inc. v. BI Inc.*, No. 11-cv-00301-DME-CBS, Alcohol Monitoring Systems, Inc.'s Reply in Support of its Motion for Summary Judgement of Non-Infrigement Regarding the '884 Patent, Doc.#79 (D. Colo. Dec. 9, 2011), 10 pages.

*Alcohol Monitoring Systems, Inc. v. BI Inc.*, No. 11-cv-00301-DME-CBS, Notice of Entry of Appearance, Doc.#80 (D. Colo. Dec. 14, 2011), 2 pages.

*Alcohol Monitoring Systems, Inc. v. BI Inc.*, No. 11-cv-00301-DME-CBS, Notice of Entry of Appearance, Doc.#81 (D. Colo. Dec. 14, 2011), 2 pages.

*Alcohol Monitoring Systems, Inc. v. BI Inc.*, No. 11-cv-00301-DME-CBS, Minute Entry for Status Conference, Doc.#82 (D. Colo. Dec. 14, 2011), 2 pages.

*Alcohol Monitoring Systems, Inc. v. BI Inc.*, No. 11-cv-00301-DME-CBS, Reporter's Transcript of Status Conference, Doc.#83 (D. Colo. Dec. 15, 2011), 51 pages.

*Alcohol Monitoring Systems, Inc. v. BI Inc.*, No. 11-cv-00301-DME-CBS, Order Setting Markman Hearing and Briefing Schedule, Doc.#84 (D. Colo. Dec. 20, 2011), 1 page.

*Alcohol Monitoring Systems, Inc. v. BI Inc.*, No. 11-cv-00301-DME-CBS, Status Report, Doc.#85 (D. Colo. Dec. 21, 2011), 6 pages.

*Alcohol Monitoring Systems, Inc. v. BI Inc.*, No. 11-cv-00301-DME-CBS, Stipulation of Dismissal of AMS's Third Claim for Relief, Doc.#86 (D. Colo. Dec. 21, 2011), 3 pages.

*Alcohol Monitoring Systems, Inc. v. BI Inc.*, No. 11-cv-00301-DME-CBS, BI's Timeline of Reexamination Proceedings, Doc.#87 (D. Colo. Dec. 21, 2011), 8 pages.

*Alcohol Monitoring Systems, Inc. v. BI Inc.*, No. 11-cv-00301-DME-CBS, Defendants' Answer to Plaintiff's First Amended Complaint, Doc.#88 (D. Colo. Dec. 27, 2011), 13 pages.

*Alcohol Monitoring Systems, Inc. v. BI Inc.*, No. 11-cv-00301-DME-CBS, Transcript of Status Conference, Doc.#89 (D. Colo. Jan. 6, 2012), 26 pages.

*Alcohol Monitoring Systems, Inc. v. BI Inc.*, No. 11-cv-00301-DME-CBS, Alcohol Monitoring System's Answer to BI Incorporated's Counterclaim, and Counterclaim, Doc.#90 (D. Colo. Jan. 12, 2012), 3 pages.

*Alcohol Monitoring Systems, Inc. v. BI Inc.*, No. 11-cv-00301-DME-CBS, Answer to Plaintiff's Counterclaims, Doc.#91 (D. Colo. Jan. 30, 2012), 3 pages.

*Alcohol Monitoring Systems, Inc. v. BI Inc.*, No. 11-cv-00301-DME-CBS, Courtroom Minutes/Minute Order, Doc.#93 (D. Colo. Feb. 28, 2012), 2 pages.

*Alcohol Monitoring Systems, Inc. v. BI Inc.*, No. 11-cv-00301-DME-CBS, Order to Show Cause, Doc.#94 (D. Colo. Mar. 23, 2012), 1 page.

*Alcohol Monitoring Systems, Inc. v. BI Inc.*, No. 11-cv-00301-DME-CBS, Joint Response to Order to Show Cause, Doc.#95 (D. Colo. Mar. 26, 2012), 4 pages.

*Alcohol Monitoring Systems, Inc. v. BI Inc.*, No. 11-cv-00301-DME-CBS, Order Discharging the Previous Order to Show Cause, Doc.#96 (D. Colo. Mar. 27, 2012), 1 page.

*Alcohol Monitoring Systems, Inc. v. BI Inc.*, No. 11-cv-00301-DME-CBS, Minute Order, Doc.#97 (D. Colo. Apr. 17, 2012), 1 page.

*Alcohol Monitoring Systems, Inc. v. BI Inc.*, No. 11-cv-00301-DME-CBS, Transcript of Telephonic Discovery Conference, Doc. #98 (D. Colo. May 1, 2012), 26 pages.

*Alcohol Monitoring Systems, Inc. v. BI Inc.*, No. 11-cv-00301-DME-CBS, Stipulation Regarding Election of Advice of Counsel Defense, Doc.#99 (D. Colo. May 4, 2012), 3 pages.

*Alcohol Monitoring Systems, Inc. v. BI Inc.*, No. 11-cv-00301-DME-CBS, Unopposed Motion to Restrict Access to Exhibits 5 and 6 to Alcohol Monitoring Systems, Inc.'s Supplement to its Motion for Summary Judgment of Non-Infringement Regarding the '884 Patent, Doc.#100 (D. Colo. May 17, 2012), 6 pages.

*Alcohol Monitoring Systems, Inc. v. BI Inc.*, No. 11-cv-00301-DME-CBS, Supplement/Amendment to Motion for Summary Judgment of Non-Infringement Regarding the '884 Patent, Doc.#101 (D. Colo. May 17, 2012), 76 pages.

*Alcohol Monitoring Systems, Inc. v. BI Inc.*, No. 11-cv-00301-DME-CBS, BI's Unopposed Motion for Leave to File Supplemental Markman Brief, Doc.#104 (D. Colo. May 21, 2012), 4 pages.

*Alcohol Monitoring Systems, Inc. v. BI Inc.*, No. 11-cv-00301-DME-CBS, Defendant BI's Supplemental Claim Construction Brief, Doc.#105 (D. Colo. May 21, 2012), 808 pages. (Uploaded in 5 parts).

*Alcohol Monitoring Systems, Inc. v. BI Inc.*, No. 11-cv-00301-DME-CBS, Order, Doc.#106 (D. Colo. May 22, 2012), 3 pages.

*Alcohol Monitoring Systems, Inc. v. BI Inc.*, No. 11-cv-00301-DME-CBS, Stipulation Regarding U.S. Pat. No. 5,220,919, Doc. #108 (D. Colo. May 24, 2012), 2 pages.

*Alcohol Monitoring Systems, Inc. v. BI Inc.*, No. 11-cv-00301-DME-CBS, Alcohol Monitoring Systems, Inc.'s Response to Defendants' Supplemental Claim Construction Brief, Doc.#109 (D. Colo. May 29, 2012), 127 pages.

*Alcohol Monitoring Systems, Inc. v. BI Inc.*, No. 11-cv-00301-DME-CBS, BI's Response to Alcohol Monitoring Systems' Supplement to its Motion for Summary Judgment of Non-Infringement Regarding the '884 Patent, Doc.#110 (D. Colo. May 29, 2012), 73 pages.

*Alcohol Monitoring Systems, Inc. v. BI Inc.*, No. 11-cv-00301-DME-CBS, Stipulation Regarding Claim Construction, Doc.#111 (D. Colo. May 31, 2012), 17 pages.

*Alcohol Monitoring Systems, Inc. v. BI Inc.*, No. 11-cv-00301-DME-CBS, Amended Stipulation Regarding Claim Construction, Doc.#112 (D. Colo. Jun. 6, 2012), 18 pages.

*Alcohol Monitoring Systems, Inc. v. BI Inc.*, No. 11-cv-00301-DME-CBS, Courtroom Minutes, Doc.#113 (D. Colo. Jun. 7, 2012), 4 pages.

*Alcohol Monitoring Systems, Inc. v. BI Inc.*, No. 11-cv-00301-DME-CBS, Courtroom Minutes, Doc.#114 (D. Colo. Jun. 8, 2012), 4 pages.

*Alcohol Monitoring Systems, Inc. v. BI Inc.*, No. 11-cv-00301-DME-CBS, Plaintiff's Supplemental Claim Construction Brief, Doc.#115 (D. Colo. Jun. 15, 2012), 9 pages.

*Alcohol Monitoring Systems, Inc. v. BI Inc.*, No. 11-cv-00301-DME-CBS, Defendant BI's Post-Hearing Brief on Claim Construction, Doc.#116 (D. Colo. Jun. 15, 2012), 30 pages.

(56) References Cited

OTHER PUBLICATIONS

*Alcohol Monitoring Systems, Inc.* v. *BI Inc.*, No. 11-cv-00301-DME-CBS, Order Granting Summary Judgment on Patent '884 and Constructing Claims in Patents '149 and '611, Doc.#117 (D. Colo. Jun. 20, 2012), 27 pages.
*Alcohol Monitoring Systems, Inc.* v. *BI Inc.*, No. 11-cv-00301-DME-CBS, Reporter's Transcript of Markman Hearing (vol. 1), Doc.#118 (D. Colo. Jun. 25, 2012), 217 pages.
*Alcohol Monitoring Systems, Inc.* v. *BI Inc.*, No. 11-cv-00301-DME-CBS, Joint Status Report, Doc.#119 (D. Colo. Jul. 18, 2012), 8 pages.
*Alcohol Monitoring Systems, Inc.* v. *BI Inc.*, No. 11-cv-00301-DME-CBS, Amended Scheduling Order, Doc.#120 (D. Colo. Jul. 25, 2012), 2 pages.
*Alcohol Monitoring Systems, Inc.* v. *BI Inc.*, No. 11-cv-00301-DME-CBS, Status Report, Doc.#121 (D. Colo. Nov. 15, 2012), 43 pages.
*Alcohol Monitoring Systems, Inc.* v. *BI Inc.*, No. 11-cv-00301-DME-CBS, Joint Motion to Amend Scheduling Order Regarding Post-Markman Deadlines, Doc.#122 (D. Colo. Dec. 4, 2012), 6 pages.
*Alcohol Monitoring Systems, Inc.* v. *BI Inc.*, No. 11-cv-00301-DME-CBS, Order Re: Joint Motion to Amend Scheduling Order Regarding Post-Markman Deadlines, Doc.#124 (D. Colo. Dec. 10, 2012), 2 pages.
*Alcohol Monitoring Systems, Inc.* v. *BI Inc.*, No. 11-cv-00301-DME-CBS, Joint Motion to Amend Scheduling Order Regarding Post-Markman Deadlines, Doc.#125 (D. Colo. Feb. 7, 2013), 6 pages.
*Alcohol Monitoring Systems, Inc.* v. *BI Inc.*, No. 11-cv-00301-DME-CBS, Order Re: Joint Motion to Amend Scheduling Order Regarding Post-Markman Deadlines, Doc.#127 (D. Colo. Feb. 12, 2013), 2 pages.
*Alcohol Monitoring Systems, Inc.* v. *BI Inc.*, No. 11-cv-00301-DME-CBS, Joint Motion to Amend Scheduling Order Regarding Post-Markman Deadlines, Doc.#128 (D. Colo. Mar. 12, 2013), 6 pages.
*Alcohol Monitoring Systems, Inc.* v. *BI Inc.*, No. 11-cv-00301-DME-CBS, Order Re: Joint Motion to Amend Scheduling Order Regarding Post-Markman Deadlines, Doc.#130 (D. Colo. Mar. 18, 2013), 2 pages.
*Alcohol Monitoring Systems, Inc.* v. *BI Inc.*, No. 11-cv-00301-DME-CBS, Joint Motion to Amend Scheduling Order Regarding Expert Witness Deposition and Dispositive Motions Deadlines, Doc.#131 (D. Colo. Jun. 3, 2013), 5 pages.
*Alcohol Monitoring Systems, Inc.* v. *BI Inc.*, No. 11-cv-00301-DME-CBS, Notice of Entry of Appearance, Doc.#134 (D. Colo. Jun. 26, 2013), 2 pages.
*Alcohol Monitoring Systems, Inc.* v. *BI Inc.*, No. 11-cv-00301-DME-CBS, Alcohol Monitoring Systems, Inc.'s Motion for Partial Summary Judgment of Validity Regarding the '149 Patent, Doc. #135 (D. Colo. Aug. 2, 2013), 63 pages.
*Alcohol Monitoring Systems, Inc.* v. *BI Inc.*, No. 11-cv-00301-DME-CBS, Defendants' Motion for Summary Judgment of Non-Infringement, Doc.#136 (D. Colo. Aug. 2, 2013), 27 pages.
*Alcohol Monitoring Systems, Inc.* v. *BI Inc.*, No. 11-cv-00301-DME-CBS, Declaration of Timothy P. Getzoff regarding Motion for Summary Judgment of Non-Infringement, Doc.#137 (D. Colo. Aug. 2, 2013), 534 pages. (Uploaded in 4 parts).
*Alcohol Monitoring Systems, Inc.* v. *BI Inc.*, No. 11-cv-00301-DME-CBS, Defendants' Motion to Restrict Public Access to Documents, Doc.#138 (D. Colo. Aug. 8, 2013), 3 pages.
*Alcohol Monitoring Systems, Inc.* v. *BI Inc.*, No. 11-cv-00301-DME-CBS, Unopposed Motion for an Extension of Time to Respond to Defendants' Motion for Summary Judgment of Non-Infringement, Doc.#139 (D. Colo. Aug. 8, 2013), 5 pages.
*Alcohol Monitoring Systems, Inc.* v. *BI Inc.*, No. 11-cv-00301-DME-CBS, Minute Order Granting Motion for Extension of Time to File Response, Doc.#141 (D. Colo. Aug. 13, 2013), 1 page.
*Alcohol Monitoring Systems, Inc.* v. *BI Inc.*, No. 11-cv-00301-DME-CBS, Defendants' Response to Plaintiff's Motion for Partial Summary Judgment of Validity Regarding the '149 Patent, Doc. #143 (D. Colo. Aug. 26, 2013), 103 pages.
*Alcohol Monitoring Systems, Inc.* v. *BI Inc.*, No. 11-cv-00301-DME-CBS, Joint Motion to Dismiss Claims Regarding U.S. Pat. No. 5,220,919 with Prejudice, Doc.#144 (D. Colo. Sep. 3, 2013), 4 pages.
*Alcohol Monitoring Systems, Inc.* v. *BI Inc.*, No. 11-cv-00301-DME-CBS, Order Granting Joint Motion to Dismiss Claims Regarding U.S. Pat. No. 5,220,919 with Prejudice, Doc.#145 (D. Colo. Sep. 6, 2013), 1 page.
*Alcohol Monitoring Systems, Inc.* v. *BI Inc.*, No. 11-cv-00301-DME-CBS, Alcohol Monitoring Systems, Inc.'s Reply in Support of Motion for Partial Summary Judgment of Validity Regarding the '149 Patent, Doc.#146 (D. Colo. Sep. 9, 2013), 5 pages.
*Alcohol Monitoring Systems, Inc.* v. *BI Inc.*, No. 11-cv-00301-DME-CBS, Plaintiff's Unopposed Motion to Restrict Public Access to Exhibits 2-5, Doc.#147 (D. Colo. Sep. 16, 2013), 3 pages.
*Alcohol Monitoring Systems, Inc.* v. *BI Inc.*, No. 11-cv-00301-DME-CBS, Defendants' Reply in Support of Motion for Summary Judgment of Non-Infringement, Doc.#154 (D. Colo. Sep. 30, 2013), 29 pages.
*Alcohol Monitoring Systems, Inc.* v. *BI Inc.*, No. 11-cv-00301-DME-CBS, Proposed Pretrial Order by Plaintiff Alcohol Monitoring Systems, Inc., Doc.#155 (D. Colo. Oct. 1, 2013), 41 pages.
*Alcohol Monitoring Systems, Inc.* v. *BI Inc.*, No. 11-cv-00301-DME-CBS, Courtroom Minutes/Minute Order, Doc.#156 (D. Colo. Oct. 8, 2013), 1 page.
*Alcohol Monitoring Systems, Inc.* v. *BI Inc.*, No. 11-cv-00301-DME-CBS, Final Pretrial Order, Doc.#157 (D. Colo. Oct. 8, 2013), 41 pages.
*Alcohol Monitoring Systems, Inc.* v. *BI Inc.*, No. 11-cv-00301-DME-CBS, Order Setting Trial Dates and Deadlines, Doc.#158 (D. Colo. Oct. 8, 2013), 5 pages.
*Alcohol Monitoring Systems, Inc.* v. *BI Inc.*, No. 11-cv-00301-DME-CBS, Notice of Change of Firm and Address, Doc.#159 (D. Colo. Oct. 14, 2013), 3 pages.
*Alcohol Monitoring Systems, Inc.* v. *BI Inc.*, No. 11-cv-00301-DME-CBS, Order Granting Summary Judgment on Patents '149 and '611 and Granting Motion for Partial Summary Judgment on Validity of the '149 Patents, Doc.#160 (D. Colo. Dec. 19, 2013), 23 pages.
*Alcohol Monitoring Systems, Inc.* v. *BI Inc.*, No. 11-cv-00301-DME-CBS, Final Judgment, Doc.#161 (D. Colo. Dec. 23, 2013), 2 pages.
*Alcohol Monitoring Systems, Inc.* v. *BI Inc.*, No. 11-cv-00301-DME-CBS, Proposed Bill of Costs by Defendant BI Incorporated, Doc.#162 (D. Colo. Jan. 6, 2014), 13 pages.
*Alcohol Monitoring Systems, Inc.* v. *BI Inc.*, No. 11-cv-00301-DME-CBS, Costs Taxed, Doc.#163 (D. Colo. Jan. 21, 2014), 1 page.
*Alcohol Monitoring Systems, Inc.* v. *BI Inc.*, No. 11-cv-00301-DME-CBS, Stipulation of Costs, Doc.#164 (D. Colo. Jan. 21, 2014), 3 pages.
*Alcohol Monitoring Systems, Inc.* v. *BI Inc.*, No. 11-cv-00301-DME-CBS, Entry of Appearance, Doc.#165 (D. Colo. Jan. 21, 2014), 2 pages.
*Alcohol Monitoring Systems, Inc.* v. *BI Inc.*, No. 11-cv-00301-DME-CBS, Plaintiff's Unopposed Motion to Restrict Public Access to Motion to Alter or Amend Judgment Under 59(e) and Exhibits A-E, Doc.#166 (D. Colo. Jan. 21, 2014), 6 pages.
*Alcohol Monitoring Systems, Inc.* v. *BI Inc.*, No. 11-cv-00301-DME-CBS, Alcohol Monitoring Systems, Inc.'s Motion to Alter or Amend Pursuant to Fed. R. Civ. P. 59(e), Doc.#168 (D. Colo. Jan. 21, 2014), 26 pages.
*Alcohol Monitoring Systems, Inc.* v. *BI Inc.*, No. 11-cv-00301-DME-CBS, Notice of Appeal, Doc.#171 (D. Colo. Jan. 22, 2014), 3 pages.
*Alcohol Monitoring Systems, Inc.* v. *BI Inc.*, No. 11-cv-00301-DME-CBS, Transmittal of a Notice of Appeal to the United States Court of Appeals for the Federal Circuit, Doc.#172 (D. Colo. Jan. 22, 2014), 77 pages.

(56) References Cited

OTHER PUBLICATIONS

*Alcohol Monitoring Systems, Inc. v. BI Inc.*, No. 11-cv-00301-DME-CBS, Defendants' Response to Alcohol Monitoring Systems, Inc.'s Motion to Alter or Amend Pursuant to Fed. R. Civ. P. 59(e), Doc.#175 (D. Colo. Feb. 14, 2014), 19 pages.

*Alcohol Monitoring Systems, Inc. v. BI Inc.*, No. 11-cv-00301-DME-CBS, Alcohol Monitoring Systems, Inc.'s Reply in Support of its Motion to Alter or Amend Pursuant to Fed. R. Civ. P. 59(e), Doc.#176 (D. Colo. Mar. 3, 2014), 11 pages.

*Alcohol Monitoring Systems, Inc. v. BI Inc.*, No. 11-cv-00301-DME-CBS, Order Granting in Part and Denying in Part Alcohol Monitoring Systems, Inc.'s Motion to Alter or Amend Pursuant to Fed. R. Civ. P. 59(e), Doc.#177 (D. Colo. Jul. 15, 2014), 15 pages.

*Alcohol Monitoring Systems, Inc. v. BI Inc.*, No. 11-cv-00301-DME-CBS, Amended Notice of Appeal, Doc.#178 (D. Colo. Aug. 14, 2014), 21 pages.

*Alcohol Monitoring Systems, Inc. v. BI Inc.*, No. 11-cv-00301-DME-CBS, Letter Transmitting Amended Notice of Appeal to the Federal Circuit, Doc.#179 (D. Colo. Aug. 14, 2014), 58 pages.

*Alcohol Monitoring Systems, Inc. v. BI Inc.*, No. 11-cv-00301-DME-CBS, Order of Federal Circuit, Doc.#180 (D. Colo. Aug. 26, 2014), 2 pages.

*Alcohol Monitoring Systems, Inc. v. BI Inc.*, No. 11-cv-00301-DME-CBS, Order of Court of Appeals for the Federal Circuit, Doc.#181 (D. Colo. Apr. 24, 2015), 2 pages.

*Alcohol Monitoring Systems, Inc. v. BI Inc.*, No. 11-cv-00301-DME-CBS, Judgment of Court of Appeals for the Federal Circuit, Doc.#182 (D. Colo. Jul. 13, 2015), 5 pages.

*Alcohol Monitoring Systems, Inc. v. BI Inc.*, No. 11-cv-00301-DME-CBS, Mandate of Court of Appeals for the Federal Circuit, Doc.#183 (D. Colo. Aug. 19, 2015), 1 pages.

\* cited by examiner

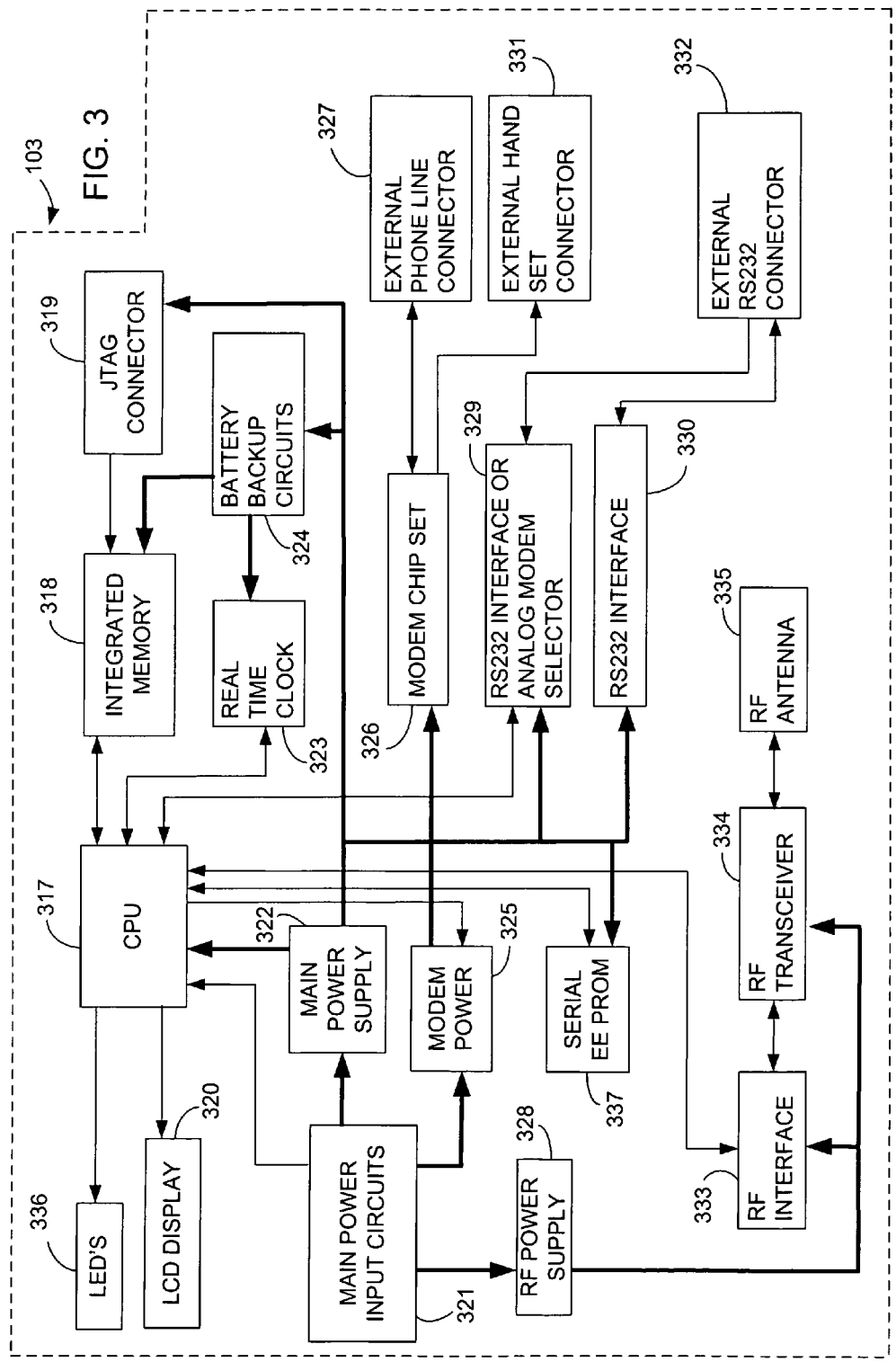

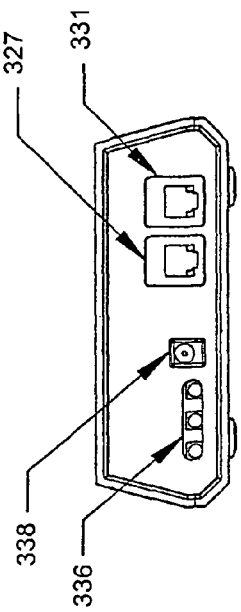
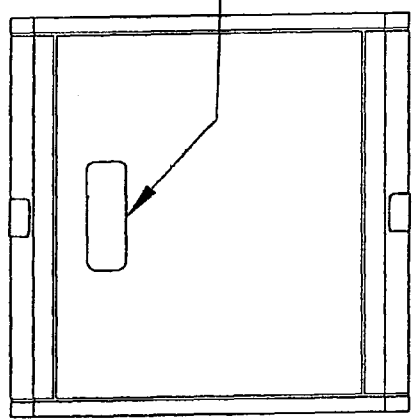
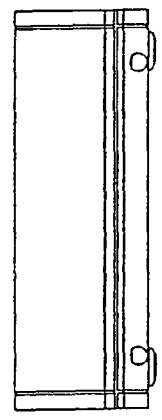
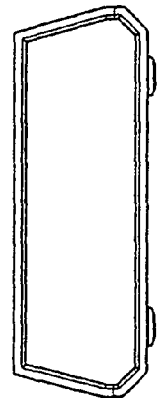
FIG. 4A
FIG. 4C
FIG. 4B
FIG. 4D

BIO-INFORMATION SENSOR MONITORING SYSTEM AND METHOD

CROSS REFERENCE TO RELATED APPLICATION

This application is a divisional application of application Ser. No. 10/441,960, filed on May 19, 2003 now U.S. Pat. No. 7,311,665, titled "BIO-INFORMATION SENSOR MONITORING SYSTEM AND METHOD," which is incorporated herein by reference in its entirety. This application is also related to a co-pending patent application Ser. No. 10/441,940 by Hawthorne et al. titled "METHOD AND APPARATUS FOR REMOTE BLOOD ALCOHOL MONITORING" and filed on May 19, 2003, now U.S. Pat. No. 7,462,149, which is owned by the same assignee of this invention.

FIELD OF THE INVENTION

This invention relates to medical monitoring systems, and more particularly, relates to an improved passive method and system for monitoring bio-information of a subject.

BACKGROUND OF THE INVENTION

In-home monitoring for the purpose of health management of chronic disease patients typically requires the patients to attach monitors of various kinds to their bodies, actuate the monitors to take various bio-information readings, and then hook up the monitor to a communication device, and then send the readings taken to a monitoring station or health care provider. Various types of monitors may be used to gather bio-information data regarding the patient. Such monitors may take the patient's blood pressure, temperature, pulse, $SpO_2$, CO, ICG, ECG, respiration, blood glucose, and the like. Such information can provide valuable feedback on the health status of the patient to the health care provider. Current technology allows for patients to take regular measurements at home that get collected and transferred, typically via a standard telephone line, to a data collection system, or directly to a health care provider. This methodology is a significant improvement over techniques that require patients to keep written logs of measurements taken themselves. Such written logs are subject to errors or missing data, and are usually only reviewed by a healthcare provider during routine checkups. In addition, some patients do not want to cooperate and take the readings that are needed, posing an additional problem to the healthcare provider.

There is a need for a remote bio-information monitoring system which can be passively used by the patient that can take the various measurements at selected time intervals as well as at random times without patient intervention. There is also a need to be able to download the bio-information measurements to a monitoring station or healthcare provider without requiring any actions on the part of the patient being monitored, eliminating the need for the patient to personally record the measurements, or connect the monitoring device to a telephone line to download and transmit the data. The present invention meets these and other needs in the art.

BRIEF DESCRIPTION OF THE DRAWINGS

FIG. 3 shows a block diagram of an embodiment of Bio-Information Modem 103.

FIGS. 4A, 4B, 4C, and 4D show a top view and three elevation views of the modem in an embodiment of the present invention.

DETAILED DESCRIPTION OF THE INVENTION

Figure 1:
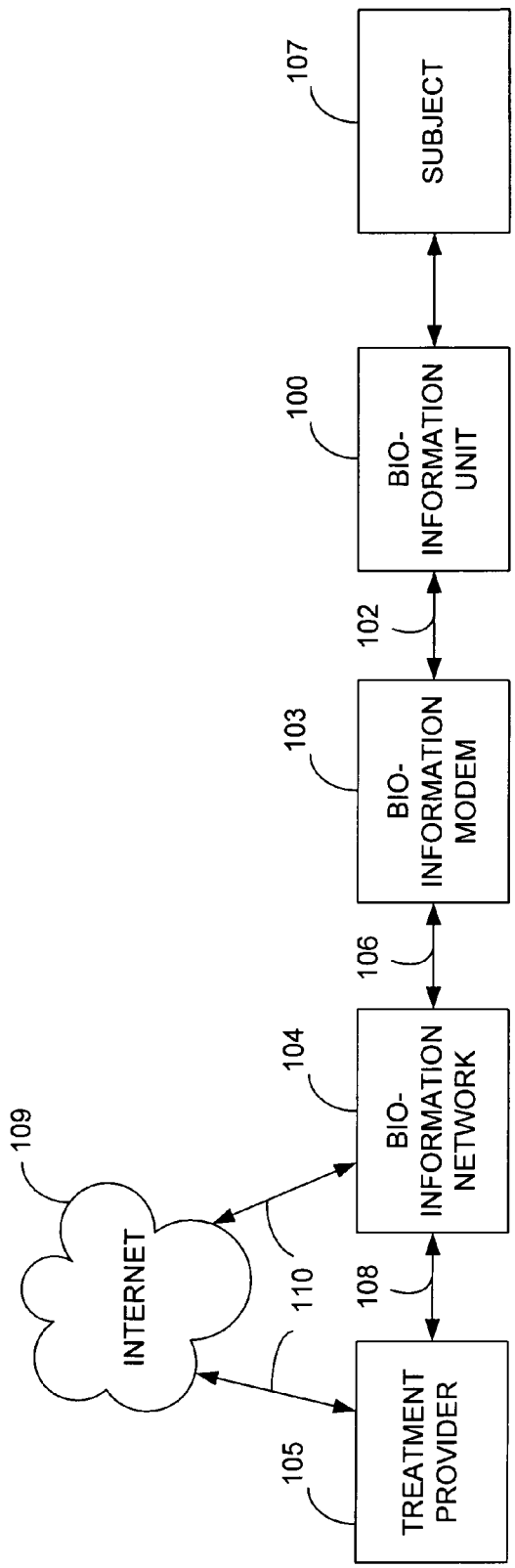
FIG. 1 shows a block diagram of the bio-information sensor monitoring system of the present invention.

FIG. 1 shows a block diagram of the bio-information sensor monitoring system of the present invention. The system and method is designed to collect, store and forward the information measured, sensed, or otherwise captured by various bio-sensors to a central web-hosted database, where treatment providers can gain access to the data collected by the bio-sensors. The system and method provides a portable means for the bio-information to be collected. The system and method can be used to remotely monitor any biological data including, but not limited to, blood oxygen, blood carbon dioxide, insulin levels, heart rate, temperature, respiration, and any other biological data based on the specific bio-sensor(s) being used in the bio-information unit. The system allows for the one or more portable bio-sensors to be worn, attached, or otherwise utilized by a subject for an extended period of time in an untethered fashion. The data collected by the bio-information unit is wirelessly forwarded to a bio-information modem that in turn forwards the collected data to a central web-hosted database where treatment providers can easily access the data collected.

Referring now to FIG. 1, a portable Bio-Information Unit 100 is worn, attached, or otherwise utilized by Subject 107 being monitored. Bio-Information Unit 100 will take readings from the one or more bio-sensors associated with it at predetermined or random intervals 24 hours a day, 7 days a week, 365 days a year. Periodically Subject 107 with Bio-Information Unit 100 comes within range of Bio-Information Modem 103. When Bio-Information Unit 100 is within range of Bio-Information Modem 103, and the timer indicates that it is time to communicate with Bio-Information Modem 103, the Bio-Information Unit 100 will transfer all the data taken from the readings collected and stored, along with any error indicators and any other diagnostic data stored to Bio-Information Modem 103. Bio-Information Modem 103 then stores all of this information for transmission to Bio-Information Network 104. After receiving all of the information from Bio-Information Unit 100, Bio-Information Modem 103 will check the stored data for any readings or errors. Either of these, or a trigger from a predetermined time interval, will cause Bio-Information Modem 103 to communicate with Bio-Information Network 104, typically through the telephone system via Communication Link 106. Once Communication Link 106 is established between Bio-Information Modem 103 and Bio-Information Network 104, Bio-Information Modem 103 will transfer all of the readings, errors, and any other diagnostic data it has stored to Bio-Information Network 104. Bio-Information Network 104 then analyzes the data received and separates and groups the data into a number of separate categories for reporting to Treatment Provider 105. The data can then be accessed by the monitoring personnel of Treatment Provider 105 through the use of secured dedicated websites through the Internet 109 and Internet Connections 110 to Bio-Information Network 104.

The communication link between Bio-Information Unit 100 and Bio-Information Modem 103 is established through a bi-directional radio frequency ("RF") Communication Link 102. RF Communication Link 102 provides a means for Bio-Information Modem 103 to set up the appropriate reading schedules and communication schedules for Bio-Information Unit 100. The reading schedules and communications schedules are set up by Treatment Provider 105 through Bio-Information Network 104. RF Communication Link 102 also provides a means for Bio-Information Modem 103 to monitor the status of the operating program of Bio-Information Unit 100, and to update this program when needed. RF Communication Link 102 also provides a means for Bio-Information Unit 100 to upload its stored readings, errors, and diagnostic data to Bio-Information Modem 103.

All of the communication between Bio-Information Modem 103 and Bio-Information Unit 100 is sent over RF Communication Link 102 in a proprietary RF encoded format. This format is similar to a standardized serial TCP/IP format with RF encoding. To ensure that the data being sent over RF Communication Link 102 is valid, each packet sent from Bio-Information Unit 100 to Bio-Information Modem 103 must be validated by Bio-Information Modem 103 before being erased from memory by Bio-Information Unit 100. The validation process insures that no data will be lost during the transfer should the transfer be interrupted by some type of interference, or if Subject 107 moves out of range of Bio-Information Modem 103 during the transfer.

Once Bio-Information Modem 103 has received all of the data from Bio-Information Unit 100, it stores the data and then checks to see if there is any information in the data received that needs to be transmitted immediately. If not, Bio-Information Modem 103 will transmit the data on scheduled is times only. Bio-Information Modem 103 is equipped with a Real Time and date Clock ("RTC") used to monitor the calendar date and the current time. This provides a means for Bio-Information Modem 103 to check on programmable schedules to see when the data should be transmitted to Bio-Information Network 104.

Once Bio-Information Modem 103 decides that it is time to transmit data to Bio-Information Network 104, it will turn off RF Communication Link 102 if it is currently on. Bio-Information Modem 103 will then turn on Modem Chip Set 326 (see FIG. 3) which is connected via a telephone line to Communication Link 106. Bio-Information Modem 103 will then check to see if a dial tone is available. If no dial tone is available, then Bio-Information Modem 103 will log an alarm indicating no dial tone, and wait a predetermined period of time, such as one minute, before attempting to dial again. Once a dial tone is established, Bio-Information Modem 103 will dial the number to connect to Bio-Information Network 104. When Bio-Information Network 104 answers the call, Modem Chip Set 326 will establish a connection via Communication Link 106. Bio-Information Network 104 will then establish communication with Bio-Information Modem 103.

Bio-Information Network 104 will first execute a series of inquiries used to validate Bio-Information Modem 103. Once Bio-Information Modem 103 is validated, Bio-Information Network 104 will then retrieve all of the information stored in Bio-Information Modem 103. Each data packet sent from Bio-Information Modem 103 must be validated by Bio-Information Network 104 before it is erased from memory by Bio-Information Modem 103. This validation process makes sure that no data will be lost during the transfer from Bio-Information Modem 103 to Bio-Information Network 104 if Communication Link 106 should be interrupted for whatever reason.

After all of the information has been received, Bio-Information Network 104 will check the status of the program stored in Bio-Information Modem 103, as well as the status of the program stored in Bio-Information Unit 100. If either program is out of date, then Bio-Information Network 104 will send an updated program to Bio-Information Modem 103, which will update the program stored in Bio-Information Unit 100 upon the next communication session with Bio-Information Unit 100. Bio-Information Network 104 will then update all schedule information for Bio-Information Modem 103 and Bio-Information Unit 100.

Bio-Information Network 104 will then sort all of the data into the appropriate categories and decide if any immediate notification action needs to be taken. If notification is needed, then Bio-Information Network 104 will perform the desired notification operations, such as sending out a page, an e-mail, a phone mail message, a fax, etc. to monitoring personnel at Treatment Provider 105 via Communication Link 108.

Treatment Provider 105 can access the data which triggered the alert by accessing the Internet 109 through Internet Connections 110 and logging into the appropriate secure web site. From the secure web site, Treatment Provider 105 can then review the alert, print reports of the desired data, as well as change any schedules or make any adjustments to the equipment operation, or contact Subject 102 if necessary.

Figure 2:
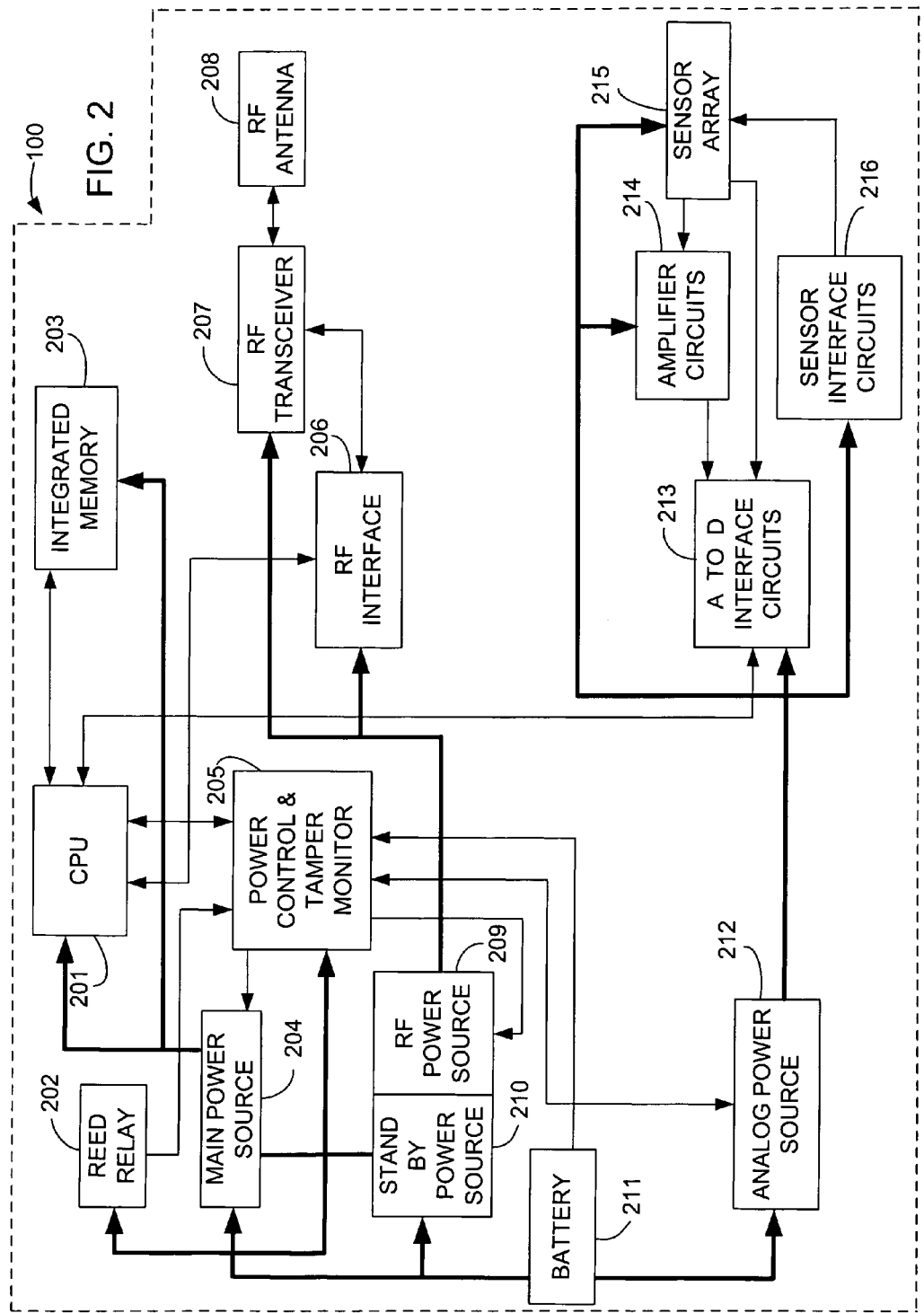
FIG. 2 shows a block diagram of the Bio-Information Unit 100 of FIG. 1.

FIG. 2 shows a block diagram of the Bio-Information Unit 100 of FIG. 1 where thicker arrows represent power circuits, and thinner arrows represent signal circuits. Referring now to FIG. 2, Bio-Information Unit 100 contains a microcontroller that functions as a Power Controller 205. Power Controller 205 controls all of the power in Bio-Information Unit 100. When the Battery 211 is inserted into Bio-Information Unit 100, Power Controller 205 is activated by Stand By Power Source 210, which causes Bio-Information Unit 100 to operate at a low voltage level. Once Power Controller 205 is initialized and running, it will turn on the main power to Bio-Information Unit 100 by activating Main Power Source 204. Power Controller 205 will then operate at the main power level with the rest of the circuits. Another function of Power Controller 205 is to monitor the output power level of Battery 211 that powers Bio-Information Unit 100. This is accomplished by running the raw battery voltage through a resistive voltage divider and then connecting it directly to Power Controller 205. Power Controller 205 also controls the power to the analog circuits and an optional analog board, (which may be present in some types of Bio-Information Units 100) through Analog Power Source 212. The optional analog board provides a means of adapting Bio-Information Unit 100 to a large assortment of bio-medical equipment. Analog Power Source 212 in turn provides the power to the Analog to Digital ("A to D") Interface Chip 213 and the Sensor Interface Circuits 216, so that the circuits are not powered up the entire time that Bio-Information Unit 100 is turned on.

Another function of Power Controller 205 is to provide a real time clock. The time and date are downloaded to CPU 201 from Bio-Information Modem 103 and are then communicated to Power Controller 205. This Process synchronizes the Bio-Information Unit 100 with the Bio-Information Modem 103. This process will occur every time the two devices communicate with each other. The Bio-Information Modem 103 also synchronizes it's time and date with the Bio-Information Network 104 each time that they communicate. Power Controller 205 will then keep track of the time and date and automatically turn on Main Power Source 204 at scheduled times, which can be programmed by CPU 201.

Power Controller 205 monitors all of the inputs that can cause Bio-Information Unit 100 to wake up due to some kind of stimulant condition existing. One condition is if a magnet is passed near Reed Relay 202. Passing a magnet near Reed Relay 202 is a method that may be employed to wake up Bio-Information Unit 100 in order to take a reading at an unscheduled time. Any such activation of Bio-Information Unit 100 is processed as an alert. Monitoring personnel can note in the records that the alert event recorded was a result of Subject 107 actions, thereby providing a means of verifying that Subject 107 took a manual reading at the appropriate time.

Passing a magnet near Reed Relay 202 will cause it to open and close creating a pulsing effect at the power controllers monitoring input. When Power Controller 205 detects this pulsing input it will immediately turn on Main Power Source 204 and activate Bio-Information Unit 100.

Bio-Information Unit 100 also contains CPU 201 which is a stand alone processor which typically has no internal memory component. In another embodiment of the invention, CPU 201 and Integrated Memory 203 may be combined together in the same chip. CPU 201 retrieves all of its instructions and data from Integrated Memory 203. Integrated Memory 203 is divided internally into several different memory segments. There is a small segment of the memory dedicated to the boot strap program. The boot strap program is used to initialize Bio-Information Unit 100 when power is first applied. The boot strap program is a very basic program that will initialize CPU 201 and then check the validity of the main operating program that is stored in a larger section of Integrated Memory 203. The boot strap program also has the capability of establishing communications through RF Communication Link 102 if the main program is not valid.

RF Communication Link 102 is established through the use of a serial to RF Transceiver 207 and RF Antenna 208. CPU 201 will command Power Controller 205 to turn on RF Power Source 209. Power Controller 205 will then activate RF Power Source 209 and supply all the RF components with low voltage. CPU 201 is connected to RF Transceiver 207 through RF Interface 206 which allows the serial signal from CPU 201 to be converted to the proper voltage for the RF transceiver circuits. By establishing RF Communication Link 102 the main program can then be downloaded into Bio-Information Unit 100 by Bio-Information Modem 103 if required. Once the boot strap program has verified that the main program is valid, it will then switch operation to the main program segment in Integrated Memory 203. If the main operating program was verified, then Bio-Information Unit 100 will switch operation to the main program segment in Integrated Memory 203 instead of establishing RF Communication Link 102.

A to D Interface Chip 213 is a programmable A to D converter in that it allows for amplifier gain to be applied to the signals that are being monitored through the use of internal Amplifier Circuits 214 and software stored in Integrated Memory 203, instead of using external hardware to amplify the signals. CPU 201 can then use software stored in Integrated Memory 203 to change the gain of all the A to D channels at any time. A to D Interface Chip 213 is used to convert data captured by Sensor Array 215. Sensor Array 215 may have one or more sensors designed to capture one or more types of bio-information as discussed above. The signals from Sensor Aria)/215 are input to A to D Interface Chip 213 in analog format and are then converted to a digital signal and communicated through a serial link to CPU 201.

After Bio-Information Unit 100 has been activated by Power Controller 205, and it has confirmed all of the memory functions are good, it will read Sensor Array 215 and record all of the resulting data from each type of sensor that is being monitored at the time. After Bio-Information Unit 100 has completed reading Sensor Array 215, it will then activate the RF circuits and wait to see if a RF signal is received from Bio-Information Modem 103. If a signal is received from Bio-Information Modem 103, Bio-Information Unit 100 will then retrieve all of the information stored in Integrated Memory 203 and transmit it to Bio-Information Modem 103. If no signal is received then Bio-Information Unit 100 will turn off until the next scheduled wake up time.

FIG. 3 shows a block diagram of an embodiment of Bio-Information Modem 103 where thicker arrows represent power circuits, and thinner arrows represent signal circuits. FIGS. 4A, 4B, 4C, and 4D show a top and three elevation views of an embodiment of Bio-Information Modem 103. Referring now to FIG. 3 and FIGS. 4A, 4B, 4C, and 4D, Bio-Information Modem 103 is powered by an external dc power supply (not shown in FIG. 3 or FIGS. 4A, 4B, 4C, and 4D). The dc power supply can be configured to plug into either a 115V AC supply or an international type power outlet. The dc power supply is plugged into an external power source and then plugged into the back of Bio-Information Modem 103 at a Main Power Input 338. Main Power Input 338 is connected to Main Power Input Circuits 321. Main Power Input Circuits 321 filter the power and make sure that the polarity of the power is correct and then distributes the power to Main Power Supply 322, Modem Power Supply 325, and RF Power Supply 328. Main Power Input Circuits 321 also monitor the power for AC power failures. This is accomplished by running the DC power input through a resistive divider and then into CPU 317.

Main Power Supply 322 supplies the power to CPU 317, RS232 Interface or Analog Modem Selector 329, RS232 Interface 330, Serial EE Prom 337, Battery Backup Circuits 324 and JTAG Connector 319. Battery Backup Circuits 324 supply the power to Integrated Memory 318 and Real Time Clock 323. The main power is applied as soon as Bio-Information Modem 103 is plugged in. The fact that Bio-Information Modem 103 is on is reflected by at least one LED that is illuminated in LED's 336. LCD Display 320 is also used to display any special instructions or request of Subject 107 by the monitoring personnel. Test results and critical sensor information can also be displayed on LCD Display 320. LCD Display 320 will also display any schedule information that Subject 107 may need to be aware of.

Integrated Memory 318 is divided internally into several different memory segments. There is a small segment of the memory dedicated to the boot strap program. The boot strap program is used to initialize Bio-Information Modem 103 when power is first applied. The boot strap is a very basic program that will initialize CPU 317 and then check the validity of the main operating program that is stored in a larger section of Integrated Memory 318. There is also an additional RAM component that supplies extra data storage capabilities. Serial EE Prom 337 is used to store all of the critical information for Bio-Information Modem 103 such as the serial number, device identification information and the phone numbers that should be called to connect to Bio-Information Network 104. Bio-Information Modem 103 will retrieve and validate all of the critical information and will then validate the main operational program. If the main operational program is valid, Bio-Information Modem 103 will switch operation from the bootstrap program to the main operational program. Once the switch is made Bio-Information Modem 103 will contact Bio-Information Network 104 and report the latest power fail. If the main operational program is not valid than Bio-Information Modem 103 will try to contact Bio-Information Network 104 and get the main operational program downloaded to itself. The JTAG Connector 319 also provides a means of programming both the modem boot strap program and the main operational program into Integrated Memory 318.

To connect to Bio-Information Network 104, Bio-Information Modem 103 will check the input from the RS232 Interface or Analog Modem Selector 329 and see if there is a serial cable attached to Bio-Information Modem 103 at External RS232 Connector 332, which is accessible by opening up the is cover of Bio-Information Modem 103. If there is, then Bio-Information Modem 103 will go into slave mode waiting for serial communications to come in through RS232 Interface 330. This mode provides a means of manually issuing commands and loading programs and or data to Bio-Information Modem 103. If there is no serial cable attached to Bio-Information Modem 103, then CPU 317 will turn on Modem Power Supply 325. After allowing Modem Chip Set 326 to power up and stabilize, CPU 317 will check for a dial tone. If no dial tone is identified, then CPU 317 will hang up and generate an alarm to indicate that the telephone line is not connected at External Phone Line Connector 327. Bio-Information Modem 103 will then try again after a predefined delay period. External Hand Set Connector 331 receives the telephone wire that comes from the telephone hand set.

Once a dial tone has been established, CPU 317 will dial the telephone number for Bio-Information Network 104. CPU 317 will then monitor Modem Chip Set 326 for an indication that a connection has been established with Bio-Information Network 104. If CPU 317 determines that the telephone line is busy, or that there is no answer, then CPU 317 will hang up and log an alarm indicating that a connection could not be established. Bio-Information Modem 103 will then wait a predefined delay period and try to make the connection again. Once the connection is established, Bio-Information Network 104 becomes the master and Bio-Information Modem 103 becomes the slave. Bio-Information Network 104 will then extract all of the pertinent information that it needs to validate Bio-Information Modem 103 and to update its status. It will then update Real Time Clock 323 so that Bio-Information Modem 103 is set to the proper time for the time zone where Bio-Information Modem 103 is currently located. Bio-Information Network 104 will then upload all data that has been stored in Bio-Information Modem 103 since the last upload. Bio-Information Network 104 then has the ability to download any number of specific monitoring instructions that need to be sent to Bio-Information Unit 100, along with all of the schedule information for Bio-Information Modem 103 and Bio-Information Unit 100. Bio-Information Network 104 will then tell Bio-Information Modem 103 to hang up and start operations.

CPU 317 will hang up and turn off the power to Modem Chip Set 326. CPU 317 will then activate the RF circuits and try to establish RF Communication Link 102. RF Communication Link 102 is established through the use of a serial to RF Transceiver 334 and the RF antenna 335. CPU 317 is connected to RF transceiver 334 through RF Interface 333 which allows the serial signal from CPU 317 to be converted to the proper voltage for the RF transceiver circuits. CPU 317 will start sending a standard message out over the RF Communication Link 102. This message is addressed to Bio-Information Unit 100, so if Bio-Information Unit 100 is within range of Bio-Information Modem 103 and Bio-Information Unit 100 is active, then Bio-Information Unit 100 will answer the message with a status message indicating that Bio-Information Unit 100 is active and operating. Bio-Information Modem 103 will then become the master and Bio-Information Unit 100 will become the slave. Bio-Information Modem 103 will extract all of the status information from Bio-Information Unit 100 and will validate the operating program and any pertinent operating data needed by Bio-Information Unit 100. Bio-Information Modem 103 will then update the real time clock in Bio-Information Unit 100 so that Bio-Information Unit 100 and Bio-Information Modem 103 are on the same time. Bio-Information Modem 103 will then extract any sensor reading information as well as any error information from Bio-Information Unit 100. Bio-Information Modem 103 will then turn off the RF signal. When the RF signal is turned off, Bio-Information Unit 100 will turn itself off and return to normal monitoring mode.

CPU 317 will then scan through the data just received and determine if any of the data needs to be sent immediately to Bio-Information Network 104. If not, then CPU 317 will wait a predefined delay period and then start the polling sequence again. If there is data that needs to be transmitted to Bio-Information Network 104 immediately, or if the time clock indicates that it is a scheduled time to call Bio-Information Network 104, then Bio-Information Modem 103 will go through the connection process and connect to Bio-Information Network 104.

Figure 5:
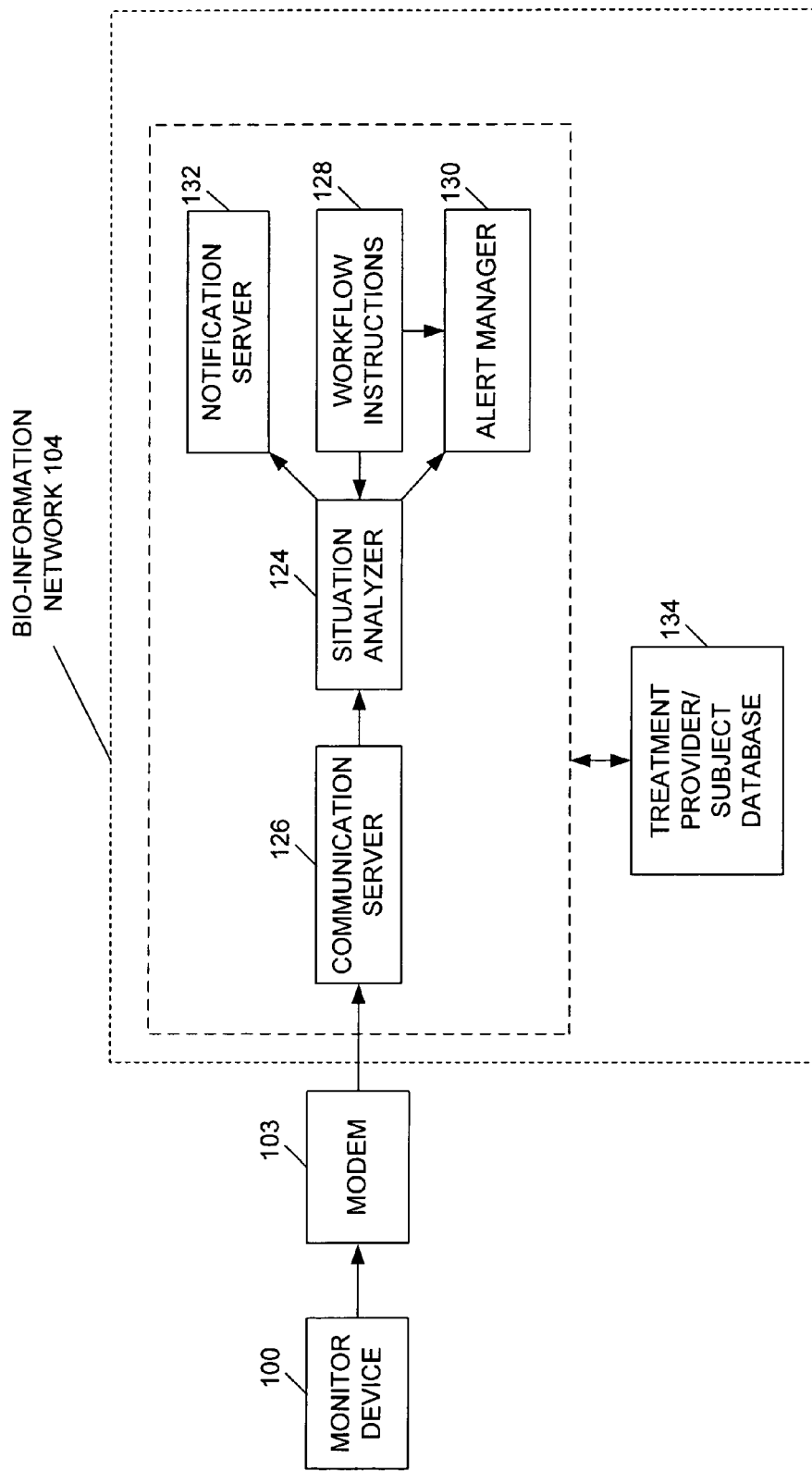
FIG. 5 shows a block diagram of the monitor network in an embodiment of the present invention.

FIG. 5 shows a more detailed block diagram of Bio-Information Network 104. Alert/sensor information is constantly being generated and monitored by the bio-information system components of the present invention. The following description will describe how and why the information is generated and how the information is handled and processed once it is generated.

Once Bio-Information Unit 100 has been adjusted properly for utilization by Subject 107, the battery pack is inserted into Bio-Information Unit 100. When the battery makes electrical contact upon being inserted into Bio-Information Unit 100, an alert is generated indicating that power has been applied to Bio-Information Unit 100. Normal occurrences of these alerts are generated each time Bio-Information Unit 100 is attached to Subject 107 or each time that the battery is changed. The power up alerts provide a means for the monitoring personnel to verify that the equipment is on Subject 107 at the appropriate times. If Subject 107 does not have the equipment on at the appropriate time the monitoring personnel can respond appropriately in case there is a problem with Subject 107. Once Bio-Information Unit 100 is operational Subject 107 simply needs to wear or attach the sensor array required and go about their normal activities. The bio-information data will be collected continuously, and transmitted automatically to the Bio-Information Modem 103.

The alert described previously will cause the Bio-Information Unit 100 to attempt to communicate with the Bio-Information Modem 103 as soon as possible, overriding the normal scheduled communications programmed in the Bio-Information Modem 103 and Bio-Information Unit 100. The bio-information system uses the scheduled communications times to ensure that all equipment is operational under normal conditions. During normal operation there should be no reason for the equipment to override the schedules, and it will only communicate when scheduled. If no schedules were used, there would be no communication and no validation that readings were being taken and stored by Bio-Information Unit 100. If Bio-Information Unit 100 does not communicate at a scheduled communications time, Bio-Information Modem 103 will generate an alert that Bio-Information Unit 100 failed to communicate on schedule, along with the present time and date. This alert will be labeled as a Communications Alert by Situation Analyzer 124. If Bio-Information Unit 100 does not communicate with Bio-Information Modem 103 for a period of 24 hours, Bio-Information Modem 103 will generate a No Communications alert, along with the present time and date. This will also be labeled as a Communications Alert by Situation Analyzer 124. Thus, the normal flow of communications between Bio-Information Unit 100 and Bio-Information Modem 103 must exist or there will be alerts generated to inform the treatment providers that something is wrong with the system.

Bio-Information Modem 103 communicates with Bio-Information Network 104 through Communication Server 126. The normal communication between these two devices is controlled by schedules programmed into the particular Bio-Information Modem 103 utilized with the particular Bio-Information Unit 100. Bio-Information network 104 also monitors these schedules. If Bio-Information Modem 103 fails to communicate when scheduled, Bio-Information Network 104 will generate a Communications Alert indicating that Bio-Information Modem 103 failed to communicate when scheduled. Thus, if the normal communications cycle between Bio-Information Modem 103 and Communication Server 126 is broken, then alerts will be generated to inform the supervising personnel that something is wrong with the system. This type of system architecture provides the means for equipment at each level of the communications chain to generate alarms. This guarantees that if a piece of equipment anywhere in the chain of communication fails, there will be an alarm to report it. This type of architecture also provides constant monitoring without any active participation by Subject 107 being monitored. Bio-Information Unit 100 automatically collects the information from Sensor Array 215 and transmits it to Bio-Information Modem 103 whenever possible, or whenever scheduled, depending on which mode of operation is programmed into Bio-Information Unit 100.

Data input and data management are handled by Treatment Provider/Subject Database 134. Treatment Provider/Subject Database 134 is actually a combination of databases that support all of the processes in the Bio-Information Network 104. Treatment Provider/Subject Database 134 includes input and management of the Bio-Information Network 104 data, the Treatment Provider/Subject data, and any specific information relating to Treatment Provider 105, and the subject or patient data, including their individual monitoring and communications schedules and the device information for the Bio-Information Modems 103 and Bio-Information Units 100 assigned to them. This information includes what type of sensor arrays are being monitored by Bio-Information Unit 100, along with the special programs needed for Bio-Information Modem 103 and Bio-Information Unit 100 to operate correctly with the desired sensor configuration. By storing the programs in Bio-Information Network 104, Bio-Information Unit 100 can be generic in nature until it is assigned to a Subject 107 and the specific sensors that are to be monitored are assigned. After assigning the sensors, Bio-Information Network 104 will then select the appropriate software program required for monitoring the sensors and use it to remotely re-program Bio-Information Unit 100, there by specializing the unit for use with the appropriate sensors.

Treatment Provider/Subject Database 134 stores all of the readings, errors, and other information that is received from all Bio-Information Modems 103 and Bio-Information Units 100 as well as any device information that needs to be stored and monitored. Treatment Provider/Subject Database 134 provides a complete historical record of all readings and alerts for all Subjects 107 being monitored in the bio-information system.

The Situation. Analyzer 124 is used to parse the data and apply a known set of rules and instructions for handling the raw data and parsing it into a limited number of categories. This includes applying any special instructions specific to the types of sensors being monitored. These categories can be broken down as follows:

Reading Data: Includes all information that has been read by the sensor arrays.

Equipment Alert: Includes Power up alarms received from the Bio-Information Unit 100, equipment failure alerts and any type of sensor malfunction information or equipment failure that is received.

Communication Alerts: Includes No Modem Communication, No Bio-Information Unit Communication, Modem missed scheduled call-in time alerts, and Bio-Information Unit missed scheduled call-in time alerts.

Equipment Maintenance: Includes alerts for scheduled maintenance, non-scheduled maintenance, and software downloads.

Equipment Assignment: Includes alerts for equipment now assigned to a subject and equipment removed from a subject.

Situation Analyzer 124 will make inquires to Workflow Instructions 128 to get direction on what is the default or specific action that should be applied to the message that was just received. Situation Analyzer 124 will then use those instructions and any historical data relating to similar messages to make a decision as to what to do with the message just received. Situation Analyzer 124 can also monitor historical data and escalate the severity of alert messages if there is a pattern emerging in the data that would require more immediate attention. Situation Analyzer 124 can also monitor historical data to detect trends in the data and then provide feedback to Subject 107 automatically by sending messages to Bio-information Modem 103 to display the feedback information on LCD Display 320. Once Situation Analyzer 124 has made its decision, it will pass the message to Alert Manager 130. Alert Manager 130 will inquire to Workflow Instructions 128 for direction on what should be done with this message. Alert Manager 130 will then present the alert information to the monitoring personnel upon request and prompt them for some type of action required to address the alert. The main categories of alert management can be broken down as:

Review/Report the information.

Take Action: by monitoring personnel or some other person in a monitoring role.

Snooze the alert.

Log all action that is required for the alert.

Change the Status of the Alert: by taking the appropriate action the alert can now be resolved. Once resolved, the database will reflect this status and remove the Alert from the new information screens.

Situation Analyzer 124 will then check to see if the message that is being dealt with requires any type of immediate notification of a treatment provider. If it does, then Situation Analyzer 124 will send the message to Notification Server 132. Notification Server 132 will then inquire to Supervising Agency/Subject Database 134 to see what method of notification is preferred by the monitoring person, and then execute the notification method, such as sending an e-mail, sending a fax, sending a phone mail message, or sending a page to the appropriate person.

Thus, the method and system of the present invention offers multiple levels of alert ranging from alerts generated by Bio-Information Unit 100, from Bio-Information Modem 103, and from Bio-Information Network 104. The flexible and changeable scheduling at the Subject 107 level allows for more timely intervention for all of the Subjects 107 being monitored who are having problems.

Having described the present invention, it will be understood by those skilled in the art that many changes in construction and circuitry and widely differing embodiments and applications of the invention will suggest themselves without departing from the scope of the present invention.

What is claimed is:

1. A bio-information modem for use with but independent from a continuous remote bio-information unit attached to a human subject, and for use with but independent from a bio-information network, the bio-information modem comprising:
    a radio frequency transceiver for communicating bi-directional radio frequency signals with the continuous remote bio-information unit when the continuous remote bio-information unit comes within range of the bio-information modem, wherein said radio frequency signals contain a plurality of data;
    a central processing unit in communication with said radio frequency transceiver, wherein said central processing unit processes said plurality of data to determine if at least one alert condition exists; and
    a bio-information modem chip set in communication with said central processing unit, wherein when said at least one alert condition exists, a non radio frequency communication link is established by said central processing unit through said bio-information modem chip set to the bio-information network, and further wherein said central processing unit communicates an alert over said non radio frequency communication link to the bio-information network independently from the continuous remote bio-information unit.

2. The bio-information modem according to claim 1 wherein said central processing unit controls a plurality of processes, said plurality of processes comprising:
    a schedule process that controls a plurality of communication events between the continuous remote bio-information unit and the bio-information modem, and between the bio-information modem and the bio-information network;
    a monitoring process that monitors said bi-directional radio frequency signals, containing said plurality of data, between the continuous remote bio-information unit and the bio-information modem; and
    an analysis process for analyzing said plurality of data for said at least one alert condition.

3. The bio-information modem according to claim 1 wherein said plurality of data further comprises:
    a set of operating instructions;
    a sensor configuration data;
    an operating data;
    a time and date synchronization information for the continuous remote bio-information unit; and
    a plurality of monitoring data received from the continuous remote bio-information unit.

4. The bio-information modem according to claim 3 wherein said central processing unit communicates through said bio-information modem chip set to the bio-information network over said non radio frequency communication link at least a one of:
    said plurality of monitoring data;
    a time and date synchronization information;
    a schedule information;
    an operating data for the continuous remote bio-information unit;
    a bio-information modem operating program information; and
    a continuous remote bio-information unit operating program.

5. The bio-information modem according to claim 3 wherein said plurality of monitoring data further comprises:
    a plurality of bio-sensor readings taken of the human subject;
    a plurality of diagnostic data; and
    when an error has been detected by the continuous remote bio-information unit, an error data.

6. The bio-information modem according to claim 1 wherein when said central processing unit communicates said alert to the bio-information network, said bio-information network analyzes said alert according to a rules-based database, and based on said analysis, said bio-information network may send an automatic alert to a treatment provider or to a designated individual over a new communication link.

7. The bio-information modem according to claim 1 further comprising:
    an LCD display connectable to said central processing unit for displaying a plurality of status messages regarding the bio-information modem, wherein said plurality of status messages are instructions to the human subject that the continuous remote bio-information unit needs to communicate with the bio-information modem or perform a type of operation.

8. The bio-information modem according to claim 1 further comprising:
    an integrated memory connectable to said central processing unit;
    a main operating program stored in said integrated memory; and
    a main power input circuits for receiving power from an external source, wherein when said power is first received, said main power input circuits provide power to said central processing unit, wherein said central processing unit checks a validity of said main operating program, wherein if said main operating program is invalid, said bio-information modem chip set attempts to establish a communication link to the bio-information network to download a valid version of said main operating program.

9. The bio-information modem according to claim 8 further comprising:
    a real time clock connectable to said central processing unit, wherein said real time clock is updated when said communication link is established with the bio-information network, and further wherein the bio-information network uploads said plurality of data from the bio-information modem.

10. The bio-information modem according to claim 8 further comprising:

a phone line connected to the bio-information modem for establishing said communication link.

11. The bio-information modem according to claim 1 wherein the continuous remote bio-information unit monitoring of the human subject may be done twenty-four hours a day, seven days a week, 365 days a year.

12. A method for using a bio-information modem to process data received from a continuous remote bio-information unit attached to a human subject, and for use with a bio-information network, the bio-information modem being independent from both the continuous remote bio-information unit and the bio-information network, the method comprising the steps of:
   (a) communicating bi-directionally with a radio frequency transceiver in the bio-information modem radio frequency signals with the continuous remote bio-information unit when the continuous remote bio-information unit comes within range of the bio-information modem, wherein said radio frequency signals contain the data;
   (b) processing, by a central processing unit located in the bio-information modem, the data to determine if at least one alert condition exists;
   (c) when said at least one alert condition exists, establishing a non radio frequency communication link by said central processing unit through a bio-information modem chip set located in the bio-information modem to a bio-information network; and
   (d) communicating by said central processing unit an alert over said non radio frequency communication link to said bio-information network independently from the continuous remote bio-information unit.

13. The method according to claim 12 further comprising the steps of:
   controlling by said central processing unit a schedule process for scheduling a plurality of communication events between the continuous remote bio-information unit and the bio-information modem, and between the bio-information modem and the bio-information network;
   controlling by said central processing unit a monitoring process that monitors said radio frequency signals, containing the data, between the continuous remote bio-information unit and the bio-information modem; and
   controlling by said central processing unit an analysis process for analyzing the data for said at least one alert condition.

14. The method according to claim 12 wherein the data further comprises:
   a set of operating instructions;
   a sensor configuration data;
   an operating data;
   a time and date synchronization information for the continuous remote bio-information unit; and
   a plurality of monitoring data received from the continuous remote bio-information unit.

15. The method according to claim 14 further comprising the steps of:
   communicating by said central processing unit through said bio-information modem chip set to the bio-information network over said non radio frequency communication link at least a one of said plurality of monitoring data, a time and date synchronization information, a schedule information, an operating data for the continuous remote bio-information unit, a bio-information modem operating program information, and a continuous remote bio-information unit operating program.

16. The method according to claim 14 wherein said plurality of monitoring data further comprises:
   a plurality of bio-sensor readings taken of the human subject;
   a plurality of diagnostic data; and
   when an error has been detected by the continuous remote bio-information unit, an error data.

17. The method according to claim 12 further comprising the steps of:
   analyzing by the bio-information network said alert according to a rules-based database; and
   based on said analysis, sending an automatic alert to a treatment provider or to a designated individual over a new communication link.

18. The method according to claim 12 further comprising the step of:
   displaying on an LCD display of the bio-information modem a plurality of status messages regarding the bio-information modem, wherein said plurality of status messages are instructions to the human subject that the continuous remote bio-information unit needs to communicate with the bio-information modem or perform a type of operation.

19. The method according to claim 12 further comprising the steps of:
   connecting the bio-information modem to a power source;
   receiving power in said central processing unit;
   checking by said central processing unit a validity of a bio-information modem main operating program for the bio-information modem stored in an integrated memory;
   checking by said central processing unit a validity of a monitoring main operating program for the continuous remote bio-information unit stored in said integrated memory;
   when at least a one of said bio-information modem main operating program and said monitoring main operating program is invalid, establishing a communication link by said bio-information modem chip set to the bio-information network;
   downloading to the bio-information modem from the bio-information network a valid version of at least a one of said bio-information modem main operating program and said monitoring main operating program;
   storing at least a one of said bio-information modem main operating program and said monitoring main operating program in said integrated memory;
   updating a real time clock of the bio-information modem; and
   uploading by the bio-information network the data from the bio-information modem.

20. The method according to claim 19 wherein said establishing step further comprises the steps of:
   (1) checking by said central processing unit for a dial tone of a phone line connected to the bio-information modem;
   (2) if no dial tone is detected, generating a no phone line connected alarm by said central processing unit;
   (3) waiting by said central processing unit a predefined period of time; and
   (4) repeating steps (1) through (3) until a dial tone is detected.

21. The method according to claim 20 further comprising the steps of:

(5) when a dial tone is detected by said central processing unit, dialing a phone number for the bio-information network;

(6) monitoring by said bio-information modem chip set if said communication link is established to the bio-information network;

(7) if at least a one of a busy signal and a no answer is detected, generating a no connection alarm by said central processing unit;

(8) waiting by said central processing unit a predefined period of time; and (9) repeating steps (5) through (8) until said communication link is established.

22. The method according to claim 21 further comprising the step of:

once said communication link is established, downloading a monitoring instructions, a schedule information for said bio-information modem, and a schedule information for the continuous remote bio-information unit for later delivery to the continuous remote bio-information unit; and downloading a hang up instruction to the bio-information modem.

23. The method according to claim 22 further comprising the steps of:

once said hang up instruction is downloaded, hanging up by said central processing unit and powering off said bio-information modem chip set;

activating said radio frequency transceiver;

communicating a standard message over said radio frequency signals to the continuous remote bio-information unit;

when the continuous remote bio-information unit is within a range of the bio-information modem, receiving an answer message over said radio frequency signals sent from the continuous remote bio-information unit;

extracting by the bio-information modem the data from the continuous remote bio-information unit;

validating by the bio-information modem an operating program of the continuous remote bio-information unit;

updating by the bio-information modem a real time clock of the continuous remote bio-information unit;

downloading said schedule information for the continuous remote bio-information unit;

terminating said radio frequency signals sent from the bio-information modem to the continuous remote bio-information unit;

when the continuous remote bio-information unit is not within said range of the bio-information modem, terminating said radio frequency signals; and waiting a predefined period of time before recommunicating said standard message over said radio frequency signals to the continuous remote bio-information unit.

24. The method according to claim 23 further comprising the steps of:

scanning by said central processing unit the data to determine if an immediate alert needs to be communicated to the bio-information network;

when said immediate alert needs to be communicated, establishing a communication link to the bio-information network; and when there is no said immediate alert to be communicated, waiting a predefined period of time before activating said radio frequency transceiver again.

25. The method according to claim 12 wherein steps (a) through (d) may be performed twenty-four hours a day, seven days a week, 365 days a year.

* * * * *